(12) United States Patent
Vidal et al.

(10) Patent No.: US 6,537,329 B1
(45) Date of Patent: Mar. 25, 2003

(54) CATIONIC 2-SULPHONYLAMINOPHENOLS, THEIR USE AS COUPLERS FOR OXIDATION DYEING, COMPOSITIONS CONTAINING THEM AND DYEING METHODS

(75) Inventors: Laurent Vidal, Paris (FR); Jean-Baptise Saunier, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/646,672

(22) PCT Filed: Jan. 21, 2000

(86) PCT No.: PCT/FR00/00142

§ 371 (c)(1),
(2), (4) Date: Dec. 15, 2000

(87) PCT Pub. No.: WO00/42971

PCT Pub. Date: Jul. 27, 2000

(30) Foreign Application Priority Data

Jan. 21, 1999 (FR) .............................................. 99 00640

(51) Int. Cl.$^7$ ................................................ A61K 7/13
(52) U.S. Cl. ....................... 8/405; 8/406; 8/407; 8/408; 8/415; 8/421; 8/424; 562/39
(58) Field of Search ........................... 8/405, 406, 407, 8/408, 415, 424, 421; 562/39

(56) References Cited

U.S. PATENT DOCUMENTS

| | | | |
|---|---|---|---|
| 3,909,190 A | * 9/1975 | Saygin ........................ | 8/10.1 |
| 4,003,699 A | 1/1977 | Rose et al. .................. | 8/10.2 |
| 4,245,028 A | 1/1981 | Fujita et al. ................ | 430/223 |
| 4,823,985 A | 4/1989 | Grollier et al. .............. | 222/1 |
| 5,061,289 A | 10/1991 | Clausen et al. ............... | 8/405 |
| 5,380,340 A | 1/1995 | Neunhoeffer et al. ........... | 8/409 |
| 5,766,576 A | 6/1998 | Löwe et al. ................... | 424/62 |

FOREIGN PATENT DOCUMENTS

| | | |
|---|---|---|
| DE | 21 56 480 | 7/1972 |
| DE | 2156480 | * 7/1972 |
| DE | 23 59 399 | 6/1975 |
| DE | 29 06 526 | 8/1979 |
| DE | 38 43 892 | 6/1990 |
| DE | 41 33 957 | 4/1993 |
| DE | 42 38 233 | 5/1994 |
| DE | 4238233 | * 5/1994 |
| DE | 195 43 988 | 5/1997 |
| EP | 0 567 172 | 10/1993 |
| FR | 2541999 | * 2/1984 |
| FR | 2 586 913 | 3/1987 |
| FR | 2 733 749 | 11/1996 |
| GB | 1 153 196 | 5/1969 |
| GB | 1 026 978 | 4/1996 |
| JP | 59-39859 | 3/1984 |
| JP | 59-46645 | 3/1984 |
| JP | 62-108859 | 5/1987 |
| JP | 2-19576 | 1/1990 |
| JP | 2-72150 | 3/1990 |
| JP | 9-110659 | 4/1997 |
| WO | WO 94/08969 | 4/1994 |
| WO | WO 94/08970 | 4/1994 |
| WO | WO 96/15765 | 5/1996 |

OTHER PUBLICATIONS

Sabine Hünsch et al., "Synthesis and Phosphorylating Properties of 2–chloro–2,3–dihydro–3(methylsulfonyl)–1,3,2–benzoxazaphosphole 2–Oxide Derivatives with Chloro Substituents on the Benzene Ring", Liebigs Ann. Chem., vol. 1994, No. 3, Mar. 1994, pp. 269–275.
English language Derwent Abstract of DE 21 56 480. Jul. 1972.
English language Derwent Abstract of DE 42 38 233. May 1994.
English language Derwent Abstract of FR 2 733 749. Nov. 1996.
English language Derwent Abstract of JP 59–39859. Mar. 1984.
English language Derwent Abstract of JP 59–46645. Mar. 1984.
English language Derwent Abstract of JP 62–108859. May 1987.
English language Derwent Abstract of JP 2–19576. Jan. 1990.
English language Derwent Abstract of JP 2–72150. Mar. 1990.
English language Derwent Abstract of JP 9–110659. Apr. 1994.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, L.L.P.

(57) ABSTRACT

The invention concerns novel cationic 2-sulphonylaminophenols of formula (I) comprising at least a cationic group Z of formula (II), their use as coupler for oxidation dyeing of keratin fibers and in particular human keratin fibers such as hair, dyeing compositions containing them combined with at least an oxidation base, and oxidation dyeing methods using them.

33 Claims, No Drawings

CATIONIC 2-SULPHONYLAMINOPHENOLS, THEIR USE AS COUPLERS FOR OXIDATION DYEING, COMPOSITIONS CONTAINING THEM AND DYEING METHODS

The invention relates to novel cationic 2-sulphonylaminophenols of formula (I) comprising at least one cationic group Z of formula (II), to their use as couplers for the oxidation dyeing of keratin fibres, and in particular of human keratin fibres such as the hair, to oxidation dye compositions containing them in combination with at least one oxidation base, and to oxidation dyeing processes using them.

It is known practice to dye keratin fibres, and in particular human hair, with dye compositions containing oxidation dye precursors, in particular ortho-phenylenediamines, para-phenylenediamines, ortho-aminophenols or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

4-Aminophenol is generally used to obtain red shades, alone or as a mixture with other bases, and in combination with suitable couplers, and para-phenylenediamines are usually used to obtain blue shades. The use of meta-phenylenediamine-based couplers, in combination with para-phenylenediamine-based couplers, usually leads to blue shades whose fastness is generally mediocre.

The Applicant has now discovered, entirely surprisingly and unexpectedly, that novel 2-sulphonylaminophenols of formula (I) defined below comprising at least one cationic group Z of formula (II) defined below are not only suitable for use as couplers, but also make it possible to obtain dye compositions which give intense colorations with a wide range of colours, and having excellent properties of resistance with respect to the various treatments to which keratin fibres may be subjected.

These discoveries form the basis of the present invention.

A first subject of the invention is thus novel 2-sulphonylaminophenols of formula (I) below, and the addition salts thereof with an acid:

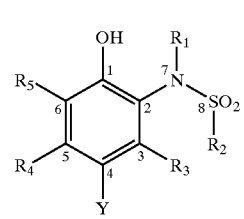

in which:
$R_1$ represents a hydrogen atom; a group Z as defined below; a linear or branched radical containing from 1 to 15 carbon atoms (it being possible for the branch(es) to form one or more 3- to 7-membered carbon-based rings) which can contain one or more double bonds and/or one or more triple bonds (the said double bonds optionally leading to aromatic groups), and one or more carbon atoms of which can be replaced with an oxygen, nitrogen or sulphur atom or with an $SO_2$ group, and the carbon atoms of which can, independently of each other, be substituted with one or more halogen atoms, the said radical $R_1$ comprising no peroxide linkages or diazo, nitro or nitroso radicals;

$R_2$ represents a hydrogen atom; a group Z as defined below; a linear or branched radical containing from 1 to 20 carbon atoms (it being possible for the branch(es) to form one or more 3- to 7-membered carbon-based rings) which can contain one or more double bonds and/or one or more triple bonds (the said double bonds optionally leading to aromatic groups), and one or more carbon atoms of which can be replaced with an oxygen, nitrogen or sulphur atom or with an $SO_2$ group, and the carbon atoms of which can, independently of each other, be substituted with one or more halogen atoms, the said radical $R_1$ comprising no peroxide linkages or diazo, nitro or nitroso radicals;

$R_3$, $R_4$ and $R_5$, which may be identical or different, represent a hydrogen or halogen atom; a group Z as defined below; a linear or branched radical containing from 1 to 20 carbon atoms (it then being possible for the branch(es) to form one or more 3- to 7-membered rings) which can contain one or more double bonds and/or one or more triple bonds (the said double bonds optionally leading to aromatic groups), and one or more carbon atoms of which can be replaced with an oxygen, nitrogen or sulphur atom or with an $SO_2$ group, and the carbon atoms of which can, independently of each other, be substituted with one or more halogen atoms, the said radical comprising no peroxide linkages or diazo, nitro or nitroso radicals; and it being understood that $R_5$ cannot represent a hydroxyl, thio or amino radical; and it being understood that the radicals $R_3$, $R_4$ and $R_5$ cannot be linked to the benzene ring of formula (I) via an —NH—NH— linkage;

Y represents a hydrogen or halogen atom; a group —$OR_6$, —$SR_6$ or —NH—$SO_2R_6$ in which $R_6$ represents a linear or branched $C_1$–$C_6$ alkyl radical (it then being possible for the branch(es) to form one or more 3- to 6-membered rings) optionally substituted with one or more radicals chosen from the group: halogen, hydroxyl, $C_1$–$C_4$ alkoxy, amino, $C_1$–$C_4$ aminoalkyl; a phenyl radical, optionally substituted with one or two radicals chosen from the group: $C_1$–$C_4$ alkyl, trifluoromethyl, carboxyl, ($C_1$–$C_4$)alkoxycarbonyl, halogen, hydroxyl, $C_1$–$C_4$ alkoxy, amino, $C_1$–$C_4$ aminoalkyl; a benzyl radical;

Z represents a cationic group represented by formula (II) below:

(II)

in which:
B represents a linear or branched $C_1$–$C_{15}$ alkyl radical (it then being possible for the branch(es) to form one or more 3- to 7-membered rings) which can contain one or more double bonds and/or one or more triple bonds, the said double bonds optionally leading to aromatic groups, and one or more carbon atoms of which can be replaced with an oxygen, nitrogen or sulphur atom or with an $SO_2$ radical, and one or more carbon atoms of which can, independently of each other, be substituted with one or more halogen atoms or with one or more groups Z, with the exclusion of peroxide linkages and diazo, nitro or nitroso radicals;
D is chosen from the groups of formulae (III) and (IV) below:

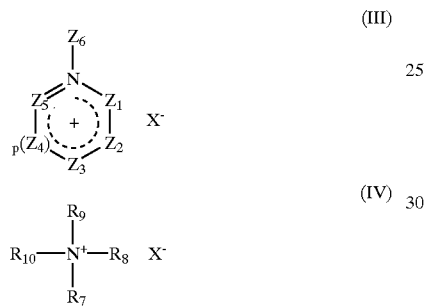

in which:
the radical B is linked to the group D by any of the atoms in the radical D;
n and p can, independently of each other, take the value 0 or 1;
when n=0, then the group (IV) can be linked to the compound of formula (I) directly via the nitrogen of the quaternary ammonium, instead of the radical $R_{10}$;
$Z_1$, $Z_2$, $Z_3$ and $Z_4$, independently of each other, represent an oxygen atom; a sulphur atom; a nitrogen atom which is unsubstituted or substituted with a radical $R_{11}$; a carbon atom which is unsubstituted or substituted with one or two radicals $R_{11}$, which may be identical or different;
$Z_5$ represents a nitrogen atom; a carbon atom which is unsubstituted or substituted with a radical $R_{11}$;
$Z_6$ can take the same meanings as those indicated below for the radical $R_{11}$; it being understood that $Z_6$ is other than a hydrogen atom;
in addition, the radicals $Z_1$ or $Z_5$ can form, with $Z_6$, a saturated or unsaturated 5- to 7-membered ring, each ring member being unsubstituted or substituted with one or two radicals $R_{11}$, which may be identical or different;
$R_{11}$ represents a hydrogen atom; a group Z; a linear or branched radical containing from 1 to 10 carbon atoms, which can contain one or more double bonds and/or one or more triple bonds, it then being possible for the said double bonds optionally to lead to aromatic groups, and one or more carbon atoms of which can be replaced with an oxygen, nitrogen or sulphur atom or with an $SO_2$ group, and one or more carbon atoms of which can, independently of each other, be substituted with one or more halogen atoms, the said radical comprising no peroxide linkages and no diazo, nitro or nitroso radicals;
two of the adjacent radicals $Z_1$, $Z_2$, $Z_3$, $Z_4$ and $Z_5$ can also form a 5- to 7-membered ring, each ring member being independently represented by:
  a carbon atom which is unsubstituted or substituted with one or two radicals $R_{11}$, which may be identical or different;
  a nitrogen atom which is unsubstituted or substituted with a radical $R_{11}$;
  an oxygen atom;
  a sulphur atom;
$R_7$, $R_8$, $R_9$ and $R_{10}$, which may be identical or different, have the same meanings as those indicated above for the radical $R_{11}$;
the radicals $R_7$, $R_8$ and $R_9$ can also form, in pairs with the quaternary nitrogen atom to which they are attached, one or more saturated 5- to 7-membered rings, each ring member being independently represented by:
  a carbon atom which is unsubstituted or substituted with one or two radicals $R_{11}$, which may be identical or different;
  a nitrogen atom which is unsubstituted or substituted with a radical $R_{11}$;
  an oxygen atom;
  a sulphur atom;
$X^-$ represents an organic or inorganic anion and is preferably chosen from the group consisting of a halide group such as chloride, bromide, fluoride or iodide; a hydroxide; a sulphate; a hydrogen sulphate; a ($C_1$–$C_6$)alkyl sulphate such as, for example, a methyl sulphate or an ethyl sulphate; an acetate; a tartrate; an oxalate; a ($C_1$–$C_6$) alkylsulphonate such as methylsulphonate; an arylsulphonate which is unsubstituted or substituted with a $C_1$–$C_4$ alkyl radical such as 4-toluylsulphonate;
it being understood that at least one of the groups $R_1$ to $R_5$ represents a group Z.

As mentioned above, the oxidation dye composition containing the compound(s) of formula (I) in accordance with the invention makes it possible to obtain intense colorations in shades ranging from red to blue which furthermore have noteworthy fastness with respect to various treatments to which keratin fibres may be subjected. These properties are particularly noteworthy especially as regards the resistance of the colorations obtained with respect to the action of light, bad weather, washing, permanent-waving and perspiration.

According to the invention, when it is indicated that one or more of the carbon atoms of the radical(s) $R_1$ to $R_8$ can be replaced with an oxygen, nitrogen or sulphur atom or with an $SO_2$ group, and/or that the said radicals $R_1$ to $R_8$ can contain one or more double bonds and/or one or more triple bonds, this means that it is possible, for example, to carry out the following conversions:

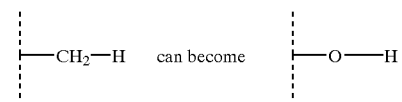

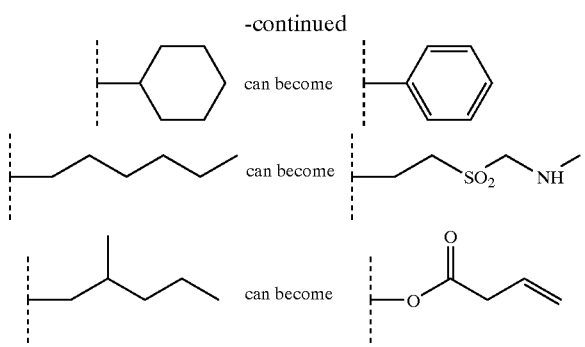

According to the invention, $R_1$ preferably denotes a hydrogen atom, a radical Z or a group $A_1$, $A_2$, $A_3$, $A_4$ or $A_5$ as defined below.

According to the invention, the term "group $A_1$" means a linear or branched $C_1$–$C_8$ alkyl radical, possibly bearing one or two double bonds or one triple bond, possibly being unsubstituted or substituted with a group chosen from a group $A_2$, a group $A_4$ and a group $A_5$, possibly being unsubstituted or substituted with one or two groups, which may be identical or different, chosen from N-($C_1$–$C_3$) alkylamino, N-($C_1$–$C_3$)alkyl-N-($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano and carboxyl groups, and possibly being unsubstituted or substituted with one or more hydroxyl, fluoro or chloro groups.

The term "group $A_2$" means an aromatic group such as phenyl or naphthyl, which may be unsubstituted or substituted with one to three groups, which may be identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups.

The term "group $A_3$" means heteroaromatic groups chosen from furyl, thienyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolyl, benzimidazolyl and benzopyrimidyl groups, optionally substituted with 1 to 3 radicals defined by linear or branched $C_1$–$C_4$ alkyl, $C_1$–$C_4$ (poly)hydroxyalkyl, carboxyl, alkoxycarbonyl, halogen, amido, amino or hydroxyl.

The term "group $A_4$" means a $C_3$–$C_7$ cycloalkyl, a norbornanyl radical optionally bearing a double bond and optionally substituted with 1 or 2 radicals defined by linear or branched $C_1$–$C_4$ alkyl, $C_1$–$C_4$ (poly)hydroxyalkyl, carboxyl, alkoxycarbonyl, halogen, amido, amino or hydroxyl.

The term "group $A_5$" means a heterocycle defined by dihydrofuryl, tetrahydrofuryl, butyrolactonyl, dihydrothienyl, tetrahydrothienyl, tetrahydrothienonyl, iminothiolane, dihydropyrrolyl, pyrrolidinyl, pyrrolidinonyl, imidazolidinonyl, imidazolidinothionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridyl, piperidyl, pentalactam, morpholinyl, pyrazoli(di)nyl, pyrimi(di)nyl, pyrazinyl, piperazinyl and azepinyl.

Among these substituents, $R_1$ preferably represents a hydrogen atom; a methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethyoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; a 2-hydroxyethyl, 2-methoxyethyl or 2-ethoxyethyl group.

Even more preferably, $R_1$ represents a hydrogen atom or a methyl radical.

According to the invention, $R_2$ preferably denotes a hydrogen atom or an amino group; a group Z; a group $A_1$, $A_2$, $A_3$, $A_4$ or $A_5$ as defined above, optionally separated from the sulphur (in position 8) of the sulphonamide function of the compound of formula (I) by an —NH— or —N-($C_1$–$C_3$) alkyl-group.

Among these substituents, $R_2$ preferably denotes a group Z; a radical chosen from the group (G1) consisting of a methyl, trifluoromethyl, ethyl, 2-chloroethyl, propyl, 3-chloropropyl, isopropyl, butyl, ethoxy, amino and dimethylamino radical.

Even more preferably, $R_2$ represents a methyl, ethyl or dimethylamino radical; or a group —$D_1$, —E—$D_1$ or —NH—E—$D_1$, in which —E— represents an arm —$(CH_2)_q$—, q being an integer equal to 1 or 2, and $D_1$ represents a group D' chosen from 3-methylimidazolidinium-1-yl, 3-(2-hydroxyethyl) imidazolidinium-1-yl, 1,2,4-triazolinium-1-yl, 1,2,4-triazolinium-4-yl, N-($C_1$–$C_4$)alkylpyrid-2-yl, N-($C_1$–$C_4$) alkylpyrid-3-yl, N-($C_1$–$C_4$)alkylpyrid-4-yl, N-(2-hydroxyethyl)pyrid-2-yl, N-(2-hydroxyethyl)pyrid-3-yl, N-(2-hydroxyethyl)pyrid-4-yl, pyrid-1-yl, tri($C_1$–$C_4$) alkylammonium-N-yl, 1-methylpiperidinium-1-yl and 1,4-dimethylpiperazinium-1-yl groups.

According to the invention, $R_3$ and $R_4$, which may be identical or different, preferably denote a hydrogen or halogen atom; a hydroxyl or amino group; a group Z; a group $A_1$, $A_4$ or $A_5$ as defined above; a group $A_1$, $A_2$, $A_3$, $A_4$ or $A_5$ as defined above and separated from the phenolic nucleus of formula (I) by an oxygen atom or by an —NH—, —N($C_1$–$C_3$)alkyl-, —O(CO)—, —NH(CO)—, —N($C_1$–$C_3$) alkyl(CO)—, —NH[C=NH]—, —NH(CO)NH—, —NH (CO)N($C_1$–$C_3$)alkyl-, —NH(CO)O—, —NHSO$_2$—, —NHSO$_2$NH— or —NHSO$_2$N($C_1$–$C_3$)alkyl-.

Among these substituents, $R_3$ preferably represents a hydrogen or chlorine atom; a group Z; a methyl, hydroxymethyl, methoxymethyl, 1-hydroxyethyl, aminomethyl or methylaminomethyl radical; a hydroxyl, methoxy or acetoxy radical; an amino, methylamino or 2-hydroxyethylamino radical; a group —NH(CO)$R_{12}$ in which $R_{12}$ represents one of the radicals listed in the group (G2) consisting of methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl; phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, 1-naphthyl, 2-naphthyl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl) methyl, (2-naphthyl) methyl; tetrahydrofur-2-yl, fur-2-yl, 5-methyl-2-

(trifluoromethyl)fur-3-yl, 2-methyl-5-phenylfur-3-yl, thien-2-yl, (thien-2-yl)methyl, 3-chlorothien-2-yl, 2,5-dichlorothien-3-yl, benzothien-2-yl, 3-chlorobenzothien-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridyl, chloropyridyl, dichloropyridyl, 5-(bromo)pyrid-3-yl, piperazin-2-yl, quinoxal-2-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl radicals; or a group —NHSO$_2$R$_{13}$ in which R$_{13}$ represents one of the radicals listed in the group (G1) as defined above.

Even more preferably, R$_3$ represents a hydrogen atom; a group —O—E—D$_2$, —NH—E—D$_2$, —CH$_2$O—E—D$_2$, —CH$_2$NH—E—D$_2$, —CH$_2$NH(CO)—D$_2$, —NH(CO)—D$_2$, —NH(CO)—E—D$_2$, —NH(CO)O—E—D$_2$, —NH(CO)NH—E—D$_2$ or —NH(SO$_2$)—E—D$_2$, in which —E— has the same meaning as that given above and D$_2$ represents a group DI as defined above; a methyl, hydroxymethyl, aminomethyl, hydroxyl, methoxy, amino or methylamino radical; a group —NH(CO)R$_{14}$ in which R$_{14}$ is chosen from the group (G3) consisting of methyl, ethyl, propyl, allyl, phenyl, tetrahydrofur-2-yl, fur-2-yl, thien-2-yl, pyridyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl radicals; or a methanesulphonylamino, ethanesulphonylamino or dimethylaminosulphonylamino group.

Among these substituents, R$_4$ preferably represents a hydrogen or chlorine atom; a group Z; a methyl, ethyl, hydroxymethyl, methoxymethyl, aminomethyl or methylaminomethyl radical; a hydroxyl, methoxy, acetoxy, amino, methylamino, N-piperidino or N-morpholino group; a group —NH(CO)R$_{15}$ in which R$_{15}$ represents one of the radicals listed in the group (G2) defined above; or a group —NHSO$_2$R$_{16}$ in which R$_{16}$ represents one of the radicals listed in the group (G1) defined above.

Even more preferably, R$_4$ represents a hydrogen or chlorine atom; a group —O—E—D$_3$, —NH—E—D$_3$, —CH$_2$O—E—D$_3$, —CH$_2$NH—E—D$_3$, —CH$_2$NH(CO)—D$_3$, —NH(CO)—D$_3$, —NH(CO)—E—D$_3$, —NH(CO)O—E—D$_3$, —NH(CO)NH—E—D$_3$ and —NH(SO$_2$)—E—D$_3$, in which —E— has the same meaning as that given above, and D$_3$ represents a group D' as defined above; a methyl, hydroxymethyl, aminomethyl, hydroxyl, methoxy, amino or methylamino radical; a group —NH(CO)R$_{17}$ in which R$_{17}$ represents one of the radicals listed in the group (G3) defined above; or a methanesulphonylamino, ethanesulphonylamino or dimethylaminosulphonylamino group.

According to the invention, R$_5$ is preferably chosen from a hydrogen or halogen atom, a group Z; a group A$_1$, A$_4$ or A$_5$ as defined above; a group A$_1$, A$_2$, A$_3$, A$_4$ or A$_5$ as defined above and separated from the phenolic nucleus in the compounds of formula (I) by an oxygen or sulphur atom or by an —NH—, —N(C$_1$–C$_3$)alkyl-, —NH(CO)—, —N(C$_1$–C$_3$)alkyl(CO)—, —NH[C=NH]—, —NH(CO)NH—, —NH(CO)N—(C$_1$–C$_3$)alkyl- or —NH(CO)O— group.

Among these substituents, R$_5$ preferably represents a hydrogen, chlorine, fluorine or bromine atom; a group Z; a methyl, trifluoromethyl, allyl, hydroxymethyl, methoxymethyl, 1-hydroxyethyl, aminomethyl, methylaminomethyl, methoxy, acetoxy or methylamino radical; a group —NH(CO)R$_{18}$ in which R$_{18}$ represents one of the radicals listed in the group (G2) defined above; or a group —NHSO$_2$R$_{19}$ in which R$_{19}$ represents one of the radicals listed in the group (G1) defined above.

Even more preferably, R$_5$ represents a hydrogen, chlorine or fluorine atom; a group —O—E—D$_4$, —NH—E—D$_4$, —CH$_2$O—E—D$_4$, —CH$_2$NH—E—D$_4$, —CH$_2$NH(CO)—D$_4$, —NH(CO)—D$_4$, —NH(CO)—E—D$_4$, —NH(CO)O—E—D$_4$, —NH(CO)NH—E—D$_4$ or —NH(SO$_2$)—E—D$_4$, in which —E— has the same meaning as that given above and D$_4$ represents a group D' as defined above; a methyl, hydroxymethyl, aminomethyl, methoxy or methylamino group; a group —NH(CO)R$_{20}$ in which R$_{20}$ represents one of the radicals listed in the group (G3) defined above; or a methanesulphonylamino, ethanesulphonylamino or dimethylaminosulphonylamino group.

According to the invention, Y is preferably chosen from a hydrogen, chlorine, fluorine or bromine atom; a methoxy, ethoxy, propoxy, benzyloxy or phenoxy group; or a —OCH$_2$CH$_2$OCH$_3$, —OCH$_2$CH$_2$OCH$_3$, —OCH$_2$CH$_2$N(CH$_3$)$_2$, —OCH$_2$(CO)OH, —OCH$_2$(CO)OCH$_3$, —OCH$_2$(CO)OC$_2$H$_5$, —SCH$_2$CH$_2$CO$_2$H or —NHSO$_2$CH$_3$ group.

Even more preferably, Y is chosen from a hydrogen or chlorine atom; a methoxy, —OCH$_2$(CO)OH or —OCH$_2$(CO)OCH$_3$ group.

Among the groups D which may be mentioned, for example, are imidazolinium, thiazolinium, oxazolinium, pyrrolinium, 1,2,3-triazolinium, 1,2,4-triazolinium, isoxazolinium, isothiazolinium, imidazolidinium, thiazolidinium, pyrazolinium, pyrazolidinium, oxazolidinium, pyrazolotriazolinium, pyrazoloimidazolinium, pyrrolotriazolinium, pyrazolopyrimidinium, pyrazolopyridinium, pyridinium, pyrimidinium, pyrazinium, triazinium, benzoimidazolinium, benzoxazolinium, benzothiazolinium, indolinium, indolidinium, isoindolinium, indazolinium, benzotriazolinium, quinolinium, tetrahydroquinolinium, benzoimidazolidinium, benzopyrimidinium, tetra(C$_1$–C$_4$)-alkylammonium, polyhydroxytetra (C$_1$–C$_4$) alkylammonium, dialkylpiperidinium, dialkylpyrrolidinium, dialkylmorpholinium, dialkylthiomorpholinium, dialkylpiperazinium, azepinium and 1,4-diazabicyclo[2,2,2]octanium.

Even more preferably, D represents a 3-methylimidazolidinium-1-yl, 3-(2-hydroxyethyl)imidazolidinium-1-yl, 1,2,4-triazolinium-1-yl, 1,2,4-triazolinium-4-yl, N—($C_1$–$C_4$)alkylpyrid-2-yl, N—($C_1$–$C_4$)alkylpyrid-3-yl, N—($C_1$–$C_4$)alkylpyrid-4-yl, N-(2-hydroxyethyl)pyrid-2-yl, N-(2-hydroxyethyl)pyrid-3-yl, N-(2-hydroxyethyl)pyrid-4-yl, pyrid-1-yl, tri($C_1$–$C_4$)alkylammonium-N-yl, 1-methylpiperidinium-1-yl, thiazolinium-3-yl or 1,4-dimethylpiperazinium-1-yl.

Among the compounds of formula (I) which are particularly preferred are those in which:

i)
- $R_1$ represents a hydrogen atom;
- $R_2$ represents a group —$D_1$, —E—$D_1$ or —NH—E—$D_1$ as defined above; a methyl, ethyl or dimethylamino radical;
- $R_3$ represents a hydroxyl, amino or methylamino radical; a group —NH(CO)$R_{21}$ in which $R_{21}$ represents a radical chosen from the group (G4) consisting of methyl, methoxymethyl, 2-carboxyethyl, methoxy, amino, ethylamino and 1-pyrrolidinyl radicals; methanesulphonylamino, ethanesulphonylamino and dimethylaminosulphonylamino radicals; a group —O—E—$D_2$, —NH—E—$D_2$, —NH(CO)—$D_2$, —NH(CO)—E—$D_2$, —NH(CO)O—E—$D_2$, —NH(CO)NH—E—$D_2$ or —NH($SO_2$)—E—$D_2$ as defined above;
- $R_4$ represents a hydrogen or chlorine atom; or a methyl group;
- $R_5$ represents a hydrogen, chlorine or fluorine atom; or a methyl group;
- Y represents a hydrogen or chlorine atom; or a methoxy or —$OCH_2$(CO)$OCH_3$ group; it being understood that at least one of the groups $R_2$ and $R_3$ contains a group Z;

ii)
- $R_1$ represents a hydrogen atom;
- $R_2$ represents a group —$D_1$, —E—$D_1$ or —NH—E—$D_1$ as defined above; or a methyl, ethyl or dimethylamino radical;
- $R_3$ represents a hydrogen atom or a methyl radical;
- $R_4$ represents a hydroxyl, amino, methylamino or —NH(CO)$R_{22}$ group in which $R_{22}$ represents one of the radicals listed in the group (G4) defined above; a methanesulphonylamino, ethanesulphonylamino or dimethylaminosulphonylamino group; or a group —O—E—$D_3$, —NH—E—$D_3$, —NH(CO)—$D_3$, —NH(CO)—E—$D_3$, —NH(CO)O—E—$D_3$, —NH(CO)NH—E—$D_3$ or —NH($SO_2$)—E—$D_3$ as defined above;
- $R_5$ represents a hydrogen, chlorine or fluorine atom or a methyl, methoxy or methylamino group;
- Y represents a hydrogen or chlorine atom or a methoxy or —$OCH_2$(CO)$OCH_3$ group; it being understood that at least one of the groups $R_2$ and $R_4$ contains a group Z;

iii)
- $R_1$ represents a hydrogen atom;
- $R_2$ represents a group —$D_1$, —E—$D_1$ or —NH—E—$D_1$ as defined above; or a methyl, ethyl or dimethylamino radical;
- $R_3$ represents a hydrogen atom or a methyl radical;
- $R_4$ represents a hydrogen or chlorine atom or a methyl, methoxy or methylamino radical;
- $R_5$ represents a methylamino group or a group —NH(CO)$R_{23}$ in which $R_{23}$ represents one of the radicals listed in the group (G4) defined above; a methanesulphonylamino, ethanesulphonylamino or dimethylaminosulphonylamino group; or a group —O—E—$D_4$, —NH—E—$D_4$, —NH(CO)—$D_4$, —NH(CO)—E—$D_4$, —NH(CO)O—E—$D_4$, —NH(CO)NH—E—$D_4$ or —NH($SO_2$)—E—$D_4$ as defined above;
- Y represents a hydrogen or chlorine atom; or a methoxy or —$OCH_2$(CO)$OCH_3$ group; it being understood that at least one of the groups $R_2$ and $R_5$ contains a group Z;

iv)
- $R_1$ represents a hydrogen atom;
- $R_2$ represents a group —$D_1$, —E—D, or —NH—E—$D_1$ as defined above;
- $R_3$ represents a hydrogen atom or a methyl radical;
- $R_4$ represents a hydrogen or chlorine atom or a methyl radical;
- $R_5$ represents a hydrogen, chlorine or fluorine atom; or a methyl radical;
- Y represents a hydrogen or chlorine atom; or a methoxy or —$OCH_2$(CO)$OCH_3$ group.

Among the compounds of formula (I) above which may be mentioned most particularly are:

3-[3-(2-hydroxyphenylsulphamoyl)propyl]-1-methyl-3H-imidazol-1-ium chloride;
3-[3-(2-hydroxy-4-methylphenylsulphamoyl)propyl]-1-methyl-3H-imidazol-1-ium chloride;
3-[3-(2-hydroxy-4-aminophenylsulphamoyl)propyl]-1-methyl-3H-imidazol-1-ium chloride;
3-[3-(2-hydroxy-4-acetylaminophenylsulphamoyl)propyl]-1-methyl-3H-imidazol-1-ium chloride;
3-[3-(2-hydroxy-4-methoxycarbonylaminophenylsulphamoyl)propyl]-1-methyl-3H-imidazol-1-ium chloride;
3-[(3-hydroxy-4-methanesulphonylaminophenylcarbamoyl)methyl]-1-methyl-3H-imidazol-1-ium chloride;
3-[(3-hydroxy-4-benzenesulphonylaminophenylcarbamoyl)methyl]-1-methyl-3H-imidazol-1-ium chloride;
3-[3-(2-hydroxy-5-chlorophenylsulphamoyl)propyl]-1-methyl-3H-imidazol-1-ium chloride;
3-[3-(2-hydroxy-4-methyl-5-chlorophenylsulphamoyl)propyl]-1-methyl-3H-imidazol-1-ium chloride;
3-[3-(2-hydroxy-4-amino-5-chlorophenylsulphamoyl)propyl]-1-methyl-3H-imidazol-1-ium chloride;
3-[3-(2-hydroxy-4-acetylamino-5-chlorophenylsulphamoyl)propyl]-1-methyl-3H-imidazol-1-ium chloride;
3-[3-(2-hydroxy-4-methoxycarbonylamino-5-chlorophenylsulphamoyl)propyl]-1-methyl-3H-imidazol-1-ium chloride;
3-[(3-hydroxy-4-methanesulphonylamino-5-chlorophenylcarbamoyl)methyl]-1-methyl-3H-imidazol-1-ium chloride;
3-[(3-hydroxy-4-benzenesulphonylamino-6-chlorophenylcarbamoyl)methyl]-1-methyl-3H-imidazol-1-ium chloride;
3-[3-(2-hydroxy-5-methoxyphenylsulphamoyl)propyl]-1-methyl-3H-imidazol-1-ium chloride;
3-[3-(2-hydroxy-4-methyl-5-methoxyphenylsulphamoyl)propyl]-1-methyl-3H-imidazol-1-ium chloride;
3-[3-(2-hydroxy-4-amino-5-methoxyphenylsulphamoyl)propyl]-1-methyl-3H-imidazol-1-ium chloride;
3-[3-(2-hydroxy-4-acetylamino-5-methoxyphenylsulphamoyl)propyl]-1-methyl-3H-imidazol-1-ium chloride;
3-[3-(2-hydroxy-4-methoxycarbonylamino-5-methoxyphenylsulphamoyl)propyl]-1-methyl-3H-imidazol-1-ium chloride;

3-[(3-hydroxy-4-methanesulphonylamino-6-methoxyphenylcarbamoyl)methyl]-1-methyl-3H-imidazol-1-ium chloride;
3-[(3-hydroxy-4-benzenesulphonylamino-6-methoxyphenylcarbamoyl)methyl]-1-methyl-3H-imidazol-1-ium chloride;
3-[3-(2-hydroxy-6-aminophenylsulphamoyl)propyl]-1-methyl-3H-imidazol-1-ium chloride;
3-[3-(2-hydroxy-6-acetylaminophenylsulphamoyl)propyl]-1-methyl-3H-imidazol-1-ium chloride;
3-[3-(2-hydroxy-4,6-diaminophenylsulphamoyl)propyl]-1-methyl-3H-imidazol-1-ium chloride;
3-[3-(2-hydroxy-4-acetylamino-6-aminophenylsulphamoyl)propyl]-1-methyl-3H-imidazol-1-ium chloride;
3-[3-(2-hydroxy-3,5-dichloro-4-methylphenylsulphamoyl)propyl]-1-methyl-3H-imidazol-1-ium chloride;
3-[3-(2-hydroxy-3,5-dichloro-4-aminophenylsulphamoyl)propyl]-1-methyl-3H-imidazol-1-ium chloride;
3-[3-(2-hydroxy-3,5-dichloro-4-acetylaminophenylsulphamoyl)propyl]-1-methyl-3H-imidazol-1-ium chloride;
3-[3-(2-hydroxy-3,5-dichloro-4-methoxycarbonylaminophenylsulphamoyl)propyl]-1-methyl-3H-imidazol-1-ium chloride;
3-[3-(2-hydroxy-3-acetylaminophenylsulphamoyl)propyl]-1-methyl-3H-imidazol-1-ium chloride;
1-[3-(2-hydroxyphenylcarbamoyl)methyl]pyridinium chloride;
1-[3-(2-hydroxy-4-methylphenylcarbamoyl)methyl]pyridinium chloride;
1-[3-(2-hydroxy-4-aminophenylcarbamoyl)methyl]pyridinium chloride;
1-[3-(2-hydroxy-4-acetylaminophenylcarbamoyl)methyl]pyridinium chloride;
1-[3-(2-hydroxy-4-methoxycarbonylaminophenylcarbamoyl)methyl]-pyridinium chloride;
1-[(3-hydroxy-4-methanesulphonylaminophenylcarbamoyl)methyl]-pyridinium chloride;
1-[(3-hydroxy-4-benzenesulphonylaminophenylcarbamoyl)methyl]-pyridinium chloride;
1-[3-(2-hydroxy-5-chlorophenylcarbamoyl)methyl]pyridinium chloride;
1-[3-(2-hydroxy-4-methyl-5-chlorophenylcarbamoyl)methyl]pyridinium chloride;
1-[3-(2-hydroxy-4-amino-5-chlorophenylcarbamoyl)methyl]pyridinium chloride;
1-[3-(2-hydroxy-4-acetylamino-5-chlorophenylcarbamoyl)methyl]pyridinium chloride;
1-[3-(2-hydroxy-4-methoxycarbonylamino-5-chlorophenylcarbamoyl)methyl]pyridinium chloride;
1-[(3-hydroxy-4-methanesulphonylamino-6-chlorophenylcarbamoyl)methyl]pyridinium chloride;
1-[(3-hydroxy-4-benzenesulphonylamino-6-chlorophenylcarbamoyl)methyl]pyridinium chloride;
1-[3-(2-hydroxy-5-methoxyphenylcarbamoyl)methyl]pyridinium chloride;
1-[3-(2-hydroxy-4-methyl-5-methoxyphenylcarbamoyl)methyl]pyridinium chloride;
1-[3-(2-hydroxy-4-amino-5-methoxyphenylcarbamoyl)methyl]pyridinium chloride;
1-[3-(2-hydroxy-4-acetylamino-5-methoxyphenylcarbamoyl)methyl]pyridinium chloride;
1-[3-(2-hydroxy-4-methoxycarbonylamino-5-methoxyphenylcarbamoyl)methyl]pyridinium chloride;
1-[(3-hydroxy-4-methanesulphonylamino-6-methoxyphenylcarbamoyl)methyl]pyridinium chloride;
1-[(3-hydroxy-4-benzenesulphonylamino-6-methoxyphenylcarbamoyl)methyl]pyridinium chloride;
1-[3-(2-hydroxy-6-aminophenylcarbamoyl)methyl]pyridinium chloride;
1-[3-(2-hydroxy-6-acetylaminophenylcarbamoyl)methyl]pyridinium chloride;
1-[3-(2-hydroxy-4,6-diaminophenylcarbamoyl)methyl]pyridinium chloride;
1-[3-(2-hydroxy-4-acetylamino-6-aminophenylcarbamoyl)methyl]pyridinium chloride;
1-[3-(2-hydroxy-3,5-dichloro-4-methylphenylcarbamoyl)methyl]pyridinium chloride;
1-[3-(2-hydroxy-3,5-dichloro-4-aminophenylcarbamoyl)methyl]pyridinium chloride;
1-[3-(2-hydroxy-3,5-dichloro-4-acetylaminophenylcarbamoyl)methyl]pyridinium chloride;
1-[3-(2-hydroxy-3,5-dichloro-4-methoxycarbonylaminophenylcarbamoyl)methyl]-pyridinium chloride;
1-[3-(2-hydroxy-3-acetylaminophenylcarbamoyl)methyl]pyridinium chloride;
1-[3-(2-hydroxyphenylsulphamoyl)propyl]-1,4-dimethylpiperazin-1-ium chloride;
1-[3-(2-hydroxy-4-methylphenylsulphamoyl)propyl]-1,4-dimethylpiperazin-1-ium chloride;
1-[3-(2-hydroxy-4-aminophenylsulphamoyl)propyl]-1,4-dimethylpiperazin-1-ium chloride;
1-[3-(2-hydroxy-4-acetylaminophenylsulphamoyl)propyl]-1,4-dimethylpiperazin-1-ium chloride;
1-[3-(2-hydroxy-4-methoxycarbonylaminophenylsulphamoyl)propyl]-1,4-dimethylpiperazin-1-ium chloride;
1-[(3-hydroxy-4-methanesulphonylaminophenylcarbamoyl)methyl]-1,4-dimethylpiperazin-1-ium chloride;
1-[(3-hydroxy-4-benzenesulphonylaminophenylcarbamoyl)methyl]-1,4-dimethylpiperazin-1-ium chloride;
1-[3-(2-hydroxy-5-chlorophenylsulphamoyl)propyl]-1,4-dimethylpiperazin-1-ium chloride;
1-[3-(2-hydroxy-4-methyl-5-chlorophenylsulphamoyl)propyl]-1,4-dimethylpiperazin-1-ium chloride;
1-[3-(2-hydroxy-4-amino-5-chlorophenylsulphamoyl)propyl]-1,4-dimethylpiperazin-1-ium chloride;
1-[3-(2-hydroxy-4-acetylamino-5-chlorophenylsulphamoyl)propyl]-1,4-dimethylpiperazin-1-ium chloride;
1-[3-(2-hydroxy-4-methoxycarbonylamino-5-chlorophenylsulphamoyl)propyl]-1,4-dimethylpiperazin-1-ium chloride;
1-[(3-hydroxy-4-methanesulphonylamino-6-chlorophenylcarbamoyl)methyl]-1,4-dimethylpiperazin-1-ium chloride;
1-[(3-hydroxy-4-benzenesulphonylamino-6-chlorophenylcarbamoyl)methyl]-1,4-dimethylpiperazin-1-ium chloride;
1-[3-(2-hydroxy-5-methoxyphenylsulphamoyl)propyl]-1,4-dimethylpiperazin-1-ium chloride;
1-[3-(2-hydroxy-4-methyl-5-methoxyphenylsulphamoyl)propyl]-1,4-dimethylpiperazin-1-ium chloride;
1-[3-(2-hydroxy-4-amino-5-methoxyphenylsulphamoyl)propyl]-1,4-dimethylpiperazin-1-ium chloride;
1-[3-(2-hydroxy-4-acetylamino-5-methoxyphenylsulphamoyl)propyl]-1,4-dimethylpiperazin-1-ium chloride;
1-[3-(2-hydroxy-4-methoxycarbonylamino-5-methoxyphenylsulphamoyl)propyl]-1,4-dimethylpiperazin-1-ium chloride;
1-[(3-hydroxy-4-methanesulphonylamino-6-methoxyphenylcarbamoyl)methyl]-1,4-dimethylpiperazin-1-ium chloride;

1-[(3-hydroxy-4-benzenesulphonylamino-6-methoxyphenylcarbamoyl)methyl]-1,4-dimethylpiperazin-1-ium chloride;
1-[3-(2-hydroxy-6-aminophenylsulphamoyl)propyl]-1,4-dimethylpiperazin-1-ium chloride;
1-[3-(2-hydroxy-6-acetylaminophenylsulphamoyl)propyl]-1,4-dimethylpiperazin-1-ium chloride;
1-[3-(2-hydroxy-4,6-diaminophenylsulphamoyl)propyl]-1,4-dimethylpiperazin-1-ium chloride;
1-[3-(2-hydroxy-4-acetylamino-6-aminophenylsulphamoyl)propyl]-1,4-dimethylpiperazin-1-ium chloride;
1-[3-(2-hydroxy-3,5-dichloro-4-methylphenylsulphamoyl)propyl]-1,4-dimethylpiperazin-1-ium chloride;
1-[3-(2-hydroxy-3,5-dichloro-4-aminophenylsulphamoyl)propyl]-1,4-dimethylpiperazin-1-ium chloride;
1-[3-(2-hydroxy-3,5-dichloro-4-acetylaminophenylsulphamoyl)propyl]-1,4-dimethylpiperazin-1-ium chloride;
1-[3-(2-hydroxy-3,5-dichloro-4-methoxycarbonylaminophenylsulphamoyl)propyl]-1,4-dimethylpiperazin-1-ium chloride;
1-[3-(2-hydroxy-3-acetylaminophenylsulphamoyl)propyl]-1,4-dimethylpiperazin-1-ium chloride;
and the addition salts thereof with an acid.

The compounds of formula (I) in accordance with the invention can be prepared according to methods that are well known in the prior art and which are described, for example, in patents or patent applications JP 59 046 645, JP 59 039 859, JP 02 072 150, JP 62 108 859, DE 4 238 233, EP 567 172, DE 2 906 526 and DE 2 156 480.

Another subject of the invention is the use of the compounds of formula (I) in accordance with the invention as couplers for the oxidation dyeing of keratin fibres, and in particular of human keratin fibres such as the hair.

The invention also relates to a composition for the oxidation dyeing of keratin fibres, and in particular of human keratin fibres such as the hair, characterized in that it comprises, in a medium which is suitable for dyeing, at least one compound of formula (I) in accordance with the invention and at least one oxidation base.

The compound(s) of formula (I) in accordance with the invention and/or the addition salt(s) thereof with an acid preferably represent(s) from 0.0005% to 12% by weight approximately relative to the total weight of the dye composition, and even more preferably from 0.005% to 6% by weight approximately relative to this weight.

The nature of the oxidation base(s) which can be used in the dye composition in accordance with the invention is not critical. They are preferably chosen from the oxidation bases conventionally used in oxidation dyeing and among which mention may be made in particular of para-phenylenediamines, bis(phenyl)alkylenediamines, para-aminophenols, ortho-aminophenols and heterocyclic bases.

Among the para-phenylenediamines which can be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines which can be mentioned more particularly, for example, are N,N'-bis(β-hydroxyethyl)—N,N'-bis(4'-aminophenyl)-1,3-diaminopropanol, N,N'-bis(β-hydroxyethyl)—N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

Among the pyridine derivatives which may be mentioned more particularly are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives which may be mentioned more particularly are the compounds described, for example, in German patent DE 2 359 399 or Japanese patents JP 88-169 571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine, pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine, and the addition salts thereof and the tautomeric forms thereof, when a tautomeric equilibrium exists, and the addition salts thereof with an acid.

Among the pyrazole derivatives which may be mentioned more particularly are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

According to the invention, the dye compositions containing one or more para-phenylenediamines and/or one or more heterocyclic oxidation bases are particularly preferred.

The oxidation base(s) preferably represent(s) from 0.0005% to 12% by weight approximately relative to the total weight of the dye composition, and even more preferably from 0.005% to 6% by weight approximately relative to this weight.

In addition to the compound(s) of formula (I) above, the dye composition in accordance with the invention can also include one or more additional couplers which can be chosen from the couplers used conventionally in oxidation dyeing and among which mention may be made in particular of meta-phenylenediamines, meta-aminophenols, meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these additional couplers preferably represent from 0.0001% to 10% by weight approximately relative to the total weight of the dye composition and even more preferably from 0.005% to 5% by weight approximately relative to this weight.

In general, the addition salts with an acid which can be used in the context of the dye compositions of the invention (compounds of formula (I), oxidation bases and additional couplers) are chosen in particular from the hydrochlorides, hydrobromides, sulphates, citrates, succinates, tartrates, lactates and acetates.

The medium which is suitable for dyeing (or the support) generally consists of water or a mixture of water and at least one organic solvent to dissolve the compounds which would not be sufficiently soluble in water. As organic solvent, mention may be made, for example, of $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1% and 40% by weight approximately relative to the total weight of the dye composition, and even more preferably between 5% and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (V) below:

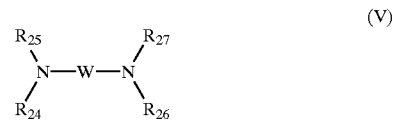

(V)

in which W is a propylene residue optionally substituted with a hydroxyl group or a $C_1$–$C_6$ alkyl radical; $R_{24}$, $R_{25}$, $R_{26}$ and $R_{27}$, which may be identical or different, represent a hydrogen atom, a $C_1$–$C_6$ alkyl radical or a $C_1$–$C_6$ hydroxyalkyl radical.

The oxidation dye compositions in accordance with the invention can also include at least one direct dye, in particular in order to modify the shades or to enrich them with glints.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for the oxidation dyeing of keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition just at the time of use, or which is present in an oxidizing composition which is applied simultaneously or sequentially.

According to one preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates and persalts such as perborates and persulphates, and enzymes such as peroxidases, laccases, tyrosinases and oxidoreductases among which mention may be made in particular of pyranose oxidases, glucose oxidases, glycerol oxidases, lactate oxidases, pyruvate oxidases and uricases.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR-2,586,913 in the name of the Applicant.

The examples which follow are intended to illustrate the invention.

PREPARATION EXAMPLE

Preparation Example 1

Synthesis of 3-[(3-hydroxy-4-methanesulphonylaminophenylcarbamoyl)methyl]-1-methyl-3H-imidazol-1-ium chloride

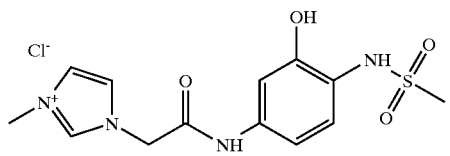

a) Preparation of N-(4-amino-2-hydroxyphenyl)methanesulphonamide hydrochloride 12 g of N-(2-hydroxy-4-nitrophenyl)methanesulphonamide (51 mmol), prepared according to Liebigs Ann. Chem. 1994, 269) in 800 ml of methanol were reduced under hydrogen (18 bar) at a temperature of 40–44° C. over 6 hours, using 2 g of palladium-on-charcoal (at a concentration of 5%, containing 50% water) as catalyst.

The filtered solution was poured into 10 ml of a methanolic hydrogen chloride solution (5.8 mol/l) and then concentrated to dryness. The powder obtained was washed twice with diisopropyl ether and dried under vacuum to constant weight, to give 11.4 g of N-(4-amino-2-hydroxyphenyl)methanesulphonamide hydrochloride in the form of a beige powder in a yield of 92%.

b) Preparation of 2-chloro-N-(3-hydroxy-4-methanesulphonylaminophenyl)acetamide 1.85 ml of chloroacetyl chloride were added dropwise, with stirring and under an inert atmosphere, to a suspension of 5.5 g of N-(4-amino-2-hydroxyphenyl)methanesulphonamide hydrochloride (23 mmol) obtained above in the preceding step and 4.6 g of calcium carbonate (46 mmol) in 150 ml of dioxane. The reaction medium was stirred at 40° C. for 5 hours, cooled to 15° C. and filtered through a sinter funnel, and the inorganic salts were rinsed twice with dioxane. The combined organic phases were concentrated, taken up in 10 ml of dioxane and poured into ice-cold water. The precipitate formed was spin-filtered and then taken up in methanol. The solution obtained was filtered through Celite and concentrated to dryness. The powder obtained was washed with dichloromethane and dried under vacuum to constant weight, to give 3.4 g of 2-chloro-N-(3-hydroxy-4-methanesulphonylaminophenyl)acetamide in the form of a beige-coloured powder, in a yield of 53%.

c) Preparation of 3-[(3-hydroxy-4-methanesulphonylaminophenylcarbamoyl)methyl]-1-methyl-3H-imidazol-1-ium chloride A solution of 2-chloro-N-(3-hydroxy-4-methanesulphonylaminophenyl)acetamide (2 g, 7.1 mmol) obtained above in the preceding step and N-methylimidazole (0.6 ml, 7.1 mmol) in 40 ml of dioxane was refluxed for 8 hours. The precipitate formed was spin-filtered, washed twice with dioxane and dried under vacuum to constant weight, to give 1.97 g of 3-[(3-hydroxy-4-methanesulphonylaminophenylcarbamoyl)methyl]-1-methyl-3H-imidazol-1-ium chloride in the form of a beige-coloured powder melting at 205° C., in a yield of 77%. The cation mass spectroscopic analysis: m/z=325 of the product obtained was in accordance with that of the expected product.

DYEING EXAMPLES

Examples 1 to 4 of Dyeing in an Alkaline Medium

The dye compositions below were prepared (contents in grams):

| EXAMPLE | 1 | 2 | 3 | 4 |
|---|---|---|---|---|
| 3-[(3-Hydroxy-4-methane-sulphonylaminophenyl-carbamoyl)methyl]-1-methyl-3H-imidazol-1-ium chloride (compound of formula (I)) | 1.087 | 1.087 | 1.087 | 1.087 |
| para-Phenylenediamine (oxidation base) | 0.324 | — | — | — |
| 4,5-Diamino-1-ethyl-3-methylpyrazole dihydrochloride (oxidation base) | — | 0.639 | — | — |
| Pyrazolo[1,5-a]pyrimidine-3,7-diamine dihydrochloride (oxidation base) | — | — | 0.666 | — |
| N,N-Bis(hydroxyethyl)-para-phenylenediamine dihydrochloride (oxidation base) | — | — | — | 0.882 |
| Common dye support No. 1 | (*) | (*) | (*) | (*) |
| Demineralized water qs | 100 g | 100 g | 100 g | 100 g |

(*) Common dye support No. 1:
| | |
|---|---|
| Benzyl alcohol | 2.0 g |
| Polyethylene glycol containing 6 mol of ethylene oxide | 3.0 g |
| 96° ethanol | 20.0 g |
| (C$_8$–C$_{10}$) Alkylpolyglucoside as an aqueous solution containing 60% active material (A.M.), buffered with ammonium citrate, sold under the name ORAMIX CG 110 ® by the company SEPPIC | 6.0 g |
| Aqueous ammonia containing 20% NH$_3$ | 10.0 g |
| Sodium metabisulphite containing 35% active material | 0.228 g |
| Pentasodium salt of diethylene-triaminepentaacetic acid | 1.1 g |

At the time of use, each of the dye compositions above was mixed weight for weight with a 20-volumes hydrogen peroxide solution (6% by weight) of pH 3.

The mixture obtained was applied to locks of natural grey hair containing 90% white hairs, for 30 minutes. The locks were then rinsed, washed with a standard shampoo, rinsed again and then dried.

The shades obtained are given in the table below:

| EXAMPLE | Dyeing pH | Shade obtained |
|---|---|---|
| 1 | 10 ± 0.2 | Ash-chestnut |
| 2 | 10 ± 0.2 | Slightly violet dark blond |
| 3 | 10 ± 0.2 | Iridescent violet-chestnut |
| 4 | 10 ± 0.2 | Blue |

What is claimed is:

1. A compound of formula (I) below and acid addition salts thereof:

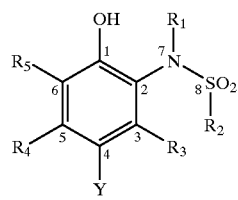

(I)

wherein:

R$_1$ represents a hydrogen atom; a group Z as defined below; a linear or branched radical containing from 1 to 15 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an SO$_2$ group, and the carbon atoms of said radical can, independently of each other, be substituted with one or more halogen atoms, with the proviso that said radical R$_1$ comprises no peroxide linkages or diazo, nitro or nitroso radicals;

R$_2$ represents a hydrogen atom; a group Z as defined below; a linear or branched radical containing from 1 to 20 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an SO$_2$ group, and the carbon atoms of said radical can, independently of each other, be substituted with one or more halogen atoms; with the proviso that said radical R$_2$ comprises no peroxide linkages or diazo, nitro or nitroso radicals;

R$_3$, R$_4$ and R$_5$, which may be identical or different, represent a hydrogen or halogen atom; a group Z as defined below; a linear or branched radical containing from 1 to 20 carbon atoms, wherein the branch(es) may form one or more 3- to 7-membered rings and wherein said radical can contain one or more double bonds and/or one or more triple bonds, wherein said double bonds may optionally lead to one or more aromatic groups, and one or more carbon atoms of said radical can be replaced with an oxygen, nitrogen or sulphur atom or with an SO$_2$ group, and the carbon atoms of said radical can, independently of each other, be substituted with one or more halogen atoms; with the provisos that said radicals R$_3$, R$_4$ and R$_5$ comprise no peroxide linkages or diazo, nitro or nitroso radicals; R$_5$ cannot represent a hydroxyl, thio or amino radical; and the radicals R$_3$, R$_4$ and R$_5$ cannot be linked to the benzene ring of formula (I) via an —NH—NH— linkage;

Y represents a hydrogen or halogen atom; a group —OR$_6$, —SR$_6$ or —NH—SO$_2$R$_6$ in which R$_6$ represents a linear or branched C$_1$–C$_6$ alkyl radical, wherein the branch(es) may form one or more 3- to 6-membered rings and wherein said linear or branched C$_1$–C$_6$ alkyl radical optionally may be substituted with one or more radicals chosen from the group: halogen, hydroxyl, C$_1$–C$_4$ alkoxy, amino, C$_1$–C$_4$ aminoalkyl; a phenyl radical, optionally substituted with one or two radicals chosen from the group: C$_1$–C$_4$ alkyl, trifluoromethyl, carboxyl, (C$_1$–C$_4$)alkoxycarbonyl, halogen, hydroxyl, C$_1$–C$_4$ alkoxy, amino, C$_1$–C$_4$ aminoalkyl; a benzyl radical;

Z represents a cationic group represented by formula (II) below:

(II)

wherein:

B represents a linear or branched C$_1$–C$_{15}$ alkyl radical, wherein the branch(es) may form one or more 3- to 7-membered rings, and wherein said linear or branched $C_1$–$C_{15}$ alkyl radical can contain one or more double bonds and/or one or more triple bonds, wherein said double bonds may optionally lead to one or more aromatic groups, and wherein one or more carbon atoms of said linear or branched $C_1$–$C_{15}$ alkyl radical can be replaced with an oxygen, nitrogen or sulphur atom or with an $SO_2$ radical; and one or more carbon atoms of said linear or branched $C_1$–$C_{15}$ alkyl radical can, independently of each other, be substituted with one or more halogen atoms or with one or more groups Z; with the proviso that B comprises no peroxide linkages or diazo, nitro or nitroso radicals;

D is chosen from the groups of formulae (III) and (IV) below:

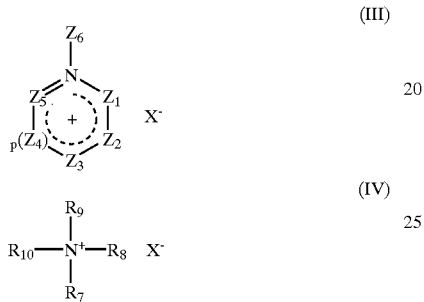

wherein:
the radical B is linked to the group D by any of the atoms in the radical D;
n and p can, independently of each other, take the value 0 or 1;
when n=0, then the group (IV) can be linked to the compound of formula (I) directly via the nitrogen of the quaternary ammonium, in place of the radical $R_{10}$;
$Z_1$, $Z_2$, $Z_3$ and $Z_4$, independently of each other, represent an oxygen atom; a sulphur atom; a nitrogen atom which is unsubstituted or substituted with a radical $R_{11}$; a carbon atom which is unsubstituted or substituted with one or two radicals $R_{11}$, which may be identical or different;
$Z_5$ represents a nitrogen atom; a carbon atom which is unsubstituted or substituted with a radical $R_{11}$;
$Z_6$ can take the same meanings as those indicated below for the radical $R_{11}$; with the proviso that $Z_6$ is not a hydrogen atom;
in addition, the radicals $Z_1$ or $Z_5$ can form, with $Z_6$, a saturated or unsaturated 5- to 7-membered ring, each ring member being unsubstituted or substituted with one or two radicals $R_{11}$, which may be identical or different;
$R_{11}$ represents a hydrogen atom; a group Z; a linear or branched radical containing from 1 to 10 carbon atoms which can contain one or more double bonds and/or one or more triple bonds, wherein said double bonds may optionally lead to one or more aromatic groups, and wherein one or more carbon atoms of said linear or branched radical can be replaced with an oxygen, nitrogen or sulphur atom or with an $SO_2$ group, and one or more carbon atoms of said linear or branched radical can, independently of each other, be substituted with one or more halogen atoms, with the proviso that said $R_{11}$ comprises no peroxide linkages and no diazo, nitro or nitroso radicals;

two of the adjacent radicals $Z_1$, $Z_2$, $Z_3$, $Z_4$ and $Z_5$ can also form a 5- to 7-membered ring, each ring member being independently represented by:
a carbon atom which is unsubstituted or substituted with one or two radicals $R_{11}$, which may be identical or different;
a nitrogen atom which is unsubstituted or substituted with a radical $R_{11}$;
an oxygen atom;
a sulphur atom;
$R_7$, $R_8$, $R_9$ and $R_{10}$, which may be identical or different, have the same meanings as those indicated above for the radical $R_{11}$;
the radicals $R_7$, $R_8$ and $R_9$ can also form, in pairs with the quaternary nitrogen atom to which they are attached, one or more saturated 5- to 7-membered rings, each ring member being independently represented by:
a carbon atom which is unsubstituted or substituted with one or two radicals $R_{11}$, which may be identical or different;
a nitrogen atom which is unsubstituted or substituted with a radical $R_{11}$;
an oxygen atom;
a sulphur atom;
$X^-$ represents an organic or inorganic anion;
with the proviso that at least one of the groups $R_1$ to $R_5$ represents a group Z.

2. A compound according to claim 1, wherein $R_1$ denotes a hydrogen atom, a radical Z; or a group $A_1$ consisting of a linear or branched $C_1$–$C_8$ alkyl radical, which can contain one or two double bonds or one triple bond, and may be unsubstituted or substituted with a group chosen from a group $A_2$, $A_4$ or $A_5$ as defined below, which may be unsubstituted or substituted with one or two groups, which may be identical or different, chosen from N—($C_1$–$C_3$)alkylamino, N—($C_1$–$C_3$)alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano and carboxyl groups, and possibly being unsubstituted or substituted with one or more hydroxyl, fluoro or chloro groups; $A_2$ consisting of an aromatic group, which may be unsubstituted or substituted with one to three groups, which may be identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups; $A_3$ consisting of heteroaromatic groups chosen from furyl, thienyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolyl and benzopyrimidyl groups, optionally substituted with 1 to 3 radicals defined by linear or branched $C_1$–$C_4$ alkyl, $C_1$–$C_4$ (poly)hydroxyalkyl, carboxyl, alkoxycarbonyl, halogen, amido, amino or hydroxyl; $A_4$ consisting of a $C_3$–$C_7$ cycloalkyl, a norbornanyl radical optionally bearing a double bond and optionally substituted with 1 or 2 radicals defined by linear or branched $C_1$–$C_4$ alkyl, $C_1$–$C_4$ (poly) hydroxyalkyl, carboxyl, alkoxycarbonyl, halogen, amido, amino or hydroxyl; or $A_5$ consisting of a heterocycle defined by dihydrofuryl, tetrahydrofuryl, butyrolactonyl, dihydrothienyl, tetrahydrothienyl, tetrahydrothienonyl, iminothiolane, dihydropyrrolyl, pyrrolidinyl, pyrrolidinonyl, imidazolidinonyl, imidazolidinothionyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridyl, piperidyl, pentalactam, morpholinyl, pyrazoli(di)nyl, pyrimi(di)nyl, pyrazinyl, piperazinyl and azepinyl.

3. A compounds according to claim 2, wherein $R_1$ represents a hydrogen atom; a methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; a 2-hydroxyethyl, 2-methoxyethyl or 2-ethoxyethyl group.

4. A compound according to claim 2, wherein $R_2$ denotes a hydrogen atom or an amino group; a group Z; a group $A_1$, $A_2$, $A_3$, $A_4$ or $A_5$, optionally separated from the sulphur (in position 8) of the sulphonamide function of the compound of formula (I) by an —NH or —N—$(C_1-C_3)$alkyl-group.

5. A compounds according to claim 2, wherein $R_2$ denotes a group Z; a radical chosen from group (G1) consisting of methyl, trifluoromethyl, ethyl, 2-chloroethyl, propyl, 3-chloropropyl, isopropyl, butyl, ethoxy, amino and dimethylamino radicals.

6. A compound according to claim 2, wherein $R_2$ represents a methyl, ethyl or dimethylamino radical; or a group —D1, —E—$D_1$ or —NH—E—$D_1$, wherein —E— represents an arm —$(CH_2)_q$—, q being an integer equal to 1 or 2, and $D_1$ represents a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—$(C_1-C_4)$alkylpyrid-2-yl, N—$(C_1-C_4)$alkylpyrid-3-yl, N—$(C_1-C_4)$alkylpyrid-4-yl, N-(2-hydroxyethyl)pyrid-2-yl, N-(2-hydroxyethyl)pyrid-3-yl, N-(2-hydroxyethyl)pyrid-4-yl, pyrid-1-yl, tri(C1–C4)alkylammonium-N-yl, 1-methylpiperidinium-1-yl and 1,4-dimethylpiperazinium-1-yl groups.

7. A compound according to claim 2, wherein $R_3$ and $R_4$, which may be identical or different, denote a hydrogen or halogen atom; a hydroxyl or amino group; a group Z; a group $A_1$, $A_4$ or $A_5$; a group $A_1$, $A_2$, $A_3$, $A_4$ or $A_5$ and separated from the phenolic nucleus of formula (I) by an oxygen atom or by an —NH—, —N$(C_1-C_3)$alkyl-, —O(CO)—, —NH(CO)—, —N$(C_1-C_3)$alkyl(CO)—, —NH[C=NH]—, —NH(CO)NH—, —NH(CO)N—$(C_1-C_3)$alkyl-, —NH(CO)O—, —NHSO$_2$—, —NHSO$_2$NH— or —NHSO$_2$N—$(C_1-C_3)$alkyl-.

8. A compound according to claim 7, wherein $R_3$ represents a hydrogen or chlorine atom; a group Z; a methyl, hydroxymethyl, methoxymethyl, 1-hydroxyethyl, aminomethyl or methylaminomethyl radical; a hydroxyl, methoxy or acetoxy radical; an amino, methylamino or 2-hydroxyethylamino radical; a group —NH(CO)$R_{12}$ in which $R_{12}$ represents a radical chosen from group (G2) consisting of methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl; phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, 1-naphthyl, 2-naphthyl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl;

tetrahydrofur-2-yl, fur-2-yl, 5-methyl-2-(trifluoromethyl)fur-3-yl, 2-methyl-5-phenylfur-3-thien-2-yl, (thien-2-yl)methyl, 3-chlorothien-2-yl, 2,5-dichlorothien-3-yl, benzothien-2-yl, 3-chlorobenzothien-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridyl, chloropyridyl, dichloropyridyl, 5-(bromo)pyrid-3-yl, piperazin-2-yl, quinoxal-2-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl radicals; or a group —NHSO$_2$R$_{13}$ in which R$_{13}$ represents a radical chosen from group (G1) consisting of a methyl, trifluoromethyl, ethyl, 2-chloroethyl, propyl, 3-chloropropyl, isopropyl, butyl, ethoxy, amino and dimethylamino radicals.

9. A compound according to claim 7, wherein $R_3$ represents a hydrogen atom; a group —O—E—$D_2$, —NH—E—$D_2$, —CH$_2$O—E—$D_2$, —CH$_2$NH—E—$D_2$, —CH$_2$NH(CO)—$D_2$, —NH(CO)—$D_2$, —NH(CO)—E—$D_2$, —NH(CO)O—E—$D_2$, —NH(CO)NH—E—$D_2$ or —NH(SO$_2$)—E—$D_2$, wherein —E— represents an arm —$(CH_2)_q$—, q being an integer equal to 1 or 2, and $D_2$ represents a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—$(C_1-C_4)$alkylpyrid-2-yl, N—$(C_1-C_4)$alkylpyrid-3-yl, N—$(C_1-C_4)$alkylpyrid-4-yl, N-(2-hydroxyethyl)pyrid-2-yl, N-(2-hydroxyethyl)pyrid-3-yl, N-(2-hydroxyethyl)pyrid-4-yl, pyrid-1-yl, tri(C1–C4)alkylammonium-N-yl, 1-methylpiperidinium-1-yl and 1,4-dimethylpiperazinium-1-yl groups; a methyl, hydroxymethyl, aminomethyl, hydroxyl, methoxy, amino or methylamino radical; a group —NH(CO)$R_{14}$ in which $R_{14}$ is chosen from group (G3) consisting of methyl, ethyl, propyl, allyl, phenyl, tetrahydrofur-2-yl, fur-2-yl, thien-2-yl, pyridyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl radicals; or a methanesulphonylamino, ethanesulphonylamino or dimethylaminosulphonylamino group.

10. A compound according to claim 7, wherein $R_4$ represents a hydrogen or chlorine atom; a group Z; a methyl, ethyl, hydroxymethyl, methoxymethyl, aminomethyl or methylaminomethyl radical; a hydroxyl, methoxy, acetoxy, amino, methylamino, N-piperidino or N-morpholino group; a group —NH(CO)$R_{15}$ in which $R_{15}$ represents a radical chosen from group (G2) consisting of methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl; phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, 1-naphthyl, 2-naphthyl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofur-2-yl, fur-2-yl, 5-methyl-2-(trifluoromethyl)fur-3-yl, 2-methyl-5-phenylfur-3-yl, thien-2-yl, (thien-2-yl)methyl, 3-chlorothien-2-yl, 2,5-dichlorothien-3-yl, benzothien-2-yl, 3-chlorobenzothien-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridyl, chloropyridyl, dichloropyridyl, 5-(bromo)pyrid-3-yl, piperazin-2-yl, quinoxal-2-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl radicals; or a group —NHSO$_2$R$_{16}$ in which R$_{16}$ represents a radical chosen from group (G1) consisting of a methyl, trifluoromethyl, ethyl, 2-chloroethyl, propyl, 3-chloropropyl, isopropyl, butyl, ethoxy, amino and dimethylamino radicals.

11. A compound according to claim 7, wherein $R_4$ represents a hydrogen or chlorine atom; a group —O—E—$D_3$, —NH—E—$D_3$, —CH$_2$O—E—$D_3$, —CH$_2$NH—E—$D_3$, —CH$_2$NH(CO)—$D_3$, —NH(CO)—$D_3$, —NH(CO)—E—$D_3$, —NH(CO)O—E—$D_3$, —NH(CO)NH—E—$D_3$ and —NH(SO$_2$)—E—$D_3$, wherein —E— represents an arm —(CH$_2$)$_q$—, q being an integer equal to 1 or 2, and $D_3$ represents a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—(C$_1$–C$_4$)alkylpyrid-2-yl, N—(C$_1$–C$_4$)alkylpyrid-3-yl, N—(C$_1$–C$_4$)alkylpyrid-4-yl, N-(2-hydroxyethyl)pyrid-2-yl, N-(2-hydroxyethyl)pyrid-3-yl, N-(2-hydroxyethyl)pyrid-4-yl, pyrid-1-yl, tri(C$_1$–C$_4$)alkylammonium-N-yl, 1-methylpiperidinium-1-yl and 1,4-dimethylpiperazinium-1-yl groups; a methyl, hydroxymethyl, aminomethyl, hydroxyl, methoxy, amino or methylamino radical; a group —NH(CO)R$_{17}$ in which R$_{17}$ represents a radical chosen from group (G3) consisting of methyl, ethyl, propyl, allyl, phenyl, tetrahydrofur-2-yl, fur-2-yl, thien-2-yl, pyridyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl radicals; or a methanesulphonylamino, ethanesulphonylamino or dimethylaminosulphonylamino group.

12. A compound according to claim 2, wherein $R_5$ is chosen from a hydrogen or halogen atom, a group Z; a group $A_1$, $A_4$ or $A_5$; a group $A_1$, $A_2$, $A_3$, $A_4$ or $A_5$ and separated from the phenolic nucleus in the compounds of formula (I) by an oxygen or sulphur atom or by an —NH—, —N(C$_1$–C$_3$)alkyl-, —NH(CO)—, —N(C$_1$–C$_3$)alkyl (CO)—, —NH[C=NH]—, —NH(CO)NH—, —NH(CO)N(C$_1$–C$_3$)alkyl- or —NH(CO)O— group.

13. A compound according to claim 2, wherein $R_5$ represents a hydrogen, chlorine, fluorine or bromine atom; a group Z; a methyl, trifluoromethyl, allyl, hydroxymethyl, methoxymethyl, 1-hydroxyethyl, aminomethyl, methylaminomethyl, methoxy, acetoxy or methylamino radical; a group —NH(CO)R$_{18}$ in which R$_{18}$ represents a radical chosen from group (G2) consisting of methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl radicals; phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, 1-naphthyl, 2-naphthyl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofur-2-yl, fur-2-yl, 5-methyl-2-(trifluoromethyl)fur-3-yl, 2-methyl-5- phenylfur-3-yl, thien-2-yl, (thien-2-yl)methyl, 3-chlorothien-2-yl, 2,5-dichlorothien-3-yl, benzothien-2-yl, 3-chlorobenzothien-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridyl, chloropyridyl, dichloropyridyl, 5-(bromo)pyrid-3-yl, piperazin-2-yl, quinoxal-2-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl radicals; or a group —NHSO2R$_{19}$ in which R$_{19}$ represents a radical chosen from group (G1) consisting of methyl, trifluoromethyl, ethyl, 2-chloroethyl, propyl, 3-chloropropyl, isopropyl, butyl, ethoxy, amino and dimethylamino radicals.

14. A compound according to claim 2, wherein R$_5$ represents a hydrogen, chlorine or fluorine atom; a group —O—E—D$_4$, —NH—E—D$_4$, —CH$_2$O—E—D$_4$, —CH$_2$NH—E—D$_4$, —CH$_2$NH(CO)—D$_4$, —NH(CO)—D$_4$, —NH(CO)—E—D$_4$, —NH(CO)O—E—D$_4$, —NH(CO)NH—E—D$_4$ or —NH(SO$_2$)—E—D$_4$, wherein —E— represents an arm —(CH$_2$)$_q$—, q being an integer equal to 1 or 2, and D$_4$ represents a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—(C$_1$–C$_4$)alkylpyrid-2-yl, N—(C$_1$–C$_4$)alkylpyrid-3-yl, N—(C$_1$–C$_4$)alkylpyrid-4-yl, N-(2-hydroxyethyl)pyrid-2-yl, N-(2-hydroxyethyl)pyrid-3-yl, N-(2-hydroxyethyl)pyrid-4-yl, pyrid-1-yl, tri(C$_1$–C$_4$)alkylammonium-N-yl, 1-methylpiperidinium-1-yl and 1,4-dimethylpiperazinium-1-yl groups; a methyl, hydroxymethyl, aminomethyl, methoxy or methylamino group; a group —NH(CO)R$_{20}$ in which R$_{20}$ represents a radical chosen from group (G3) consisting of methyl, ethyl, propyl, allyl, phenyl, tetrahydrofur-2-yl, fur-2-yl, thien-2-yl, pyridyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl radicals; or a methanesulphonylamino, ethanesulphonylamino or dimethylaminosulphonylamino group.

15. A compound according to any one of claims 1 to 14, wherein Y is chosen from a hydrogen, chlorine, fluorine or bromine atom; a methoxy, ethoxy, propoxy, benzyloxy or phenoxy group; or an —OCH$_2$CH$_2$OCH$_3$, —OCH$_2$CH$_2$OCH$_3$, —OCH$_2$CH$_2$N(CH$_3$)$_2$, —OCH$_2$(CO)OH, —OCH$_2$(CO)OCH$_3$, —OCH$_2$(CO)OC$_2$H$_5$, —SCH$_2$CH$_2$CO$_2$H or —NHSO$_2$CH$_3$ group.

16. A compound according to any one of claims 1 to 14, wherein D is chosen from imidazolinium, thiazolinium, oxazolinium, pyrrolinium, 1,2,3-triazolinium, 1,2,4-triazolinium, isoxazolinium, isothiazolinium, imidazolidinium, thiazolidinium, pyrazolinium, pyrazolidinium, oxazolidinium, pyrazoltriazolinium, pyrazoloimidazolinium, pyrrolotriazolinium, pyrazolopyrimidinium, pyrazolopyridinium, pyridinium, pyrimidinium, pyrazinium, triazinium, benzoimidazolinium, benzoxazolinium, benzothiazolinium, indolinium, indolidinium, isoindolinium, indazolinium, benzotriazolinium, quinolinium, tetrahydroquinolinium, benzoimidazolidinium, benzopyrimidinium, (C$_1$–C$_4$) tetraalkylammonium, polyhydroxytetra(C$_1$–C$_4$) alkylammonium, dialkylpiperidinium, dialkylpyrrolidinium, dialkylmorpholinium, dialkylthiomorpholinium, dialkylpiperazinium, azepinium and 1,4-diazabicyclo[2,2,2] octanium.

17. A compound according to any one of claims 1 to 14, wherein D represents a 3-methylimidazolidinium-1-yl, 3-(2-hydroxyethyl)imidazolidinium-1-yl, 1,2,4-triazolinium-1-yl, 1,2,4-triazolinium-4-yl, N—(C1–C4)alkylpyrid-2-yl, N—(C1–C4)alkylpyrid-3-yl, N—(C1–C4)alkylpyrid-4-yl, N-(2-hydroxyethyl)pyrid-2-yl, N-(2-hydroxyethyl)pyrid-3-yl, N-(2-hydroxyethyl)pyrid-4-yl, pyrid-1-yl, (C1–C4) trialkylammonium-N-yl, 1-methylpiperidinium-1-yl, thiazolinium-3-yl or 1,4-dimethylpiperazinium-1-yl group.

18. A compound according to any one of the claims 1 to 14, wherein said compound is chosen from those in which:
i)
R$_1$ represents a hydrogen atom;
R$_2$ represents a group —D$_1$, —E—D$_1$ or —NH—E—D$_1$; a methyl, ethyl or dimethylamino radical;
R$_3$ represents a hydroxyl, amino or methylamino radical; a group —NH(CO)R$_{21}$ in which R$_{21}$ represents a radical chosen from group (G4) consisting of methyl, methoxymethyl, 2-carboxyethyl, methoxy, amino, ethylamino and 1-pyrrolidinyl radicals; methanesulphonylamino, ethanesulphonylamino and dimethylaminosulphonylamino radicals; a group —O—E—D$_2$, —NH—E—D$_2$, —NH(CO)—D$_2$, —NH(CO)—E—D$_2$, —NH(CO)O—E—D$_2$, —NH(CO)NH—E—D$_2$ or —NH(SO$_2$)—E—D$_2$;
R$_4$ represents a hydrogen or chlorine atom; or a methyl group;
R$_5$ represents a hydrogen, chlorine or fluorine atom; or a methyl group;
Y represents a hydrogen or chlorine atom; or a methoxy or —OCH$_2$(CO)OCH$_3$ group; with the proviso that at least one of the groups R$_2$ and R$_3$ contains a group Z;
ii)
R$_1$ represents a hydrogen atom;
R$_2$ represents a group —D$_1$, —E—D$_1$ or —NH—E—D$_1$; or a methyl, ethyl or dimethylamino radical;
R$_3$ represents a hydrogen atom or a methyl radical;
R$_4$ represents a hydroxyl, amino, methylamino or —NH(CO)R$_{22}$ group in which R$_{22}$ represents a radical chosen from the group (G4) defined above; a methanesulphonylamino, ethanesulphonylamino or dimethylaminosulphonylamino group; or a group —O—E—$D_3$, —NH—E—$D_3$, —NH(CO)—$D_3$, —NH(CO)—E—$D_3$, —NH(CO)O—E—$D_3$, —NH(CO)O—E—$D_3$, —NH(CO)NH—E—$D_3$ or —NH($SO_2$)—E—$D_3$;

$R_5$ represents a hydrogen, chlorine or fluorine atom or a methyl, methoxy or methylamino group;

Y represents a hydrogen or chlorine atom or a methoxy or —$OCH_2(CO)OCH_3$ group; with the proviso that at least one of the groups $R_2$ and $R_4$ contains a group Z;

iii)
$R_1$ represents a hydrogen atom;
$R_2$ represents a group —$D_1$, —E—$D_1$ or —NH—E—$D_1$; or a methyl, ethyl or dimethylamino radical;
$R_3$ represents a hydrogen atom or a methyl radical;
$R_4$ represents a hydrogen or chlorine atom or a methyl, methoxy or methylamino radical;
$R_5$ represents a methylamino group or a group —NH(CO)$R_{23}$ in which $R_{23}$ represents a radical chosen from the group (G4) defined above; a methanesulphonylamino, ethanesulphonylamino or dimethylaminosulphonylamino group; or a group —O—E—$D_4$, —NH—E—$D_4$, —NH(CO)—$D_4$, —NH(CO)—E—$D_4$, —NH(CO)O—E—$D_4$, —NH(CO)NH—E—$D_4$ or —NH($SO_2$)—E—$D_4$;

Y represents a hydrogen or chlorine atom; or a methoxy or —$OCH_2(CO)OCH_3$ group; with the proviso that at least one of the groups $R_2$ and $R_5$ contains a group Z; or iv)
$R_1$ represents a hydrogen atom;
$R_2$ represents a group —$D_1$, —E—$D_1$ or —NH—E—$D_1$;
$R_3$ represents a hydrogen atom or a methyl radical;
$R_4$ represents a hydrogen or chlorine atom or a methyl radical;
$R_5$ represents a hydrogen, chlorine or fluorine atom; or a methyl radical;
Y represents a hydrogen or chlorine atom or a methoxy or —$OCH_2(CO)OCH_3$ group;

wherein —E— represents an arm —$(CH_2)_q$—, q being an integer equal to 1 or 2, and $D_1$, $D_2$, $D_3$, and $D_4$ each individually represents a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—($C_1$–$C_4$)alkylpyrid-2-yl, N—($C_1$–$C_4$)alkylpyrid-3-yl, N—($C_{1-C_4}$)alkylpyrid-4-yl, N-(2-hydroxyethyl)pyrid-2-yl, N-(2-hydroxyethyl)pyrid-3-yl, N-(2-hydroxyethyl)pyrid-4-yl, pyrid-1-yl, tri(C1–C4)alkylammonium-N-yl, 1-methylpiperidinium-1-yl and 1,4-dimethylpiperazinium-1-yl groups.

19. A compound chosen from:
3-[3-(2-hydroxyphenylsulphamoyl)propyl]-1-methyl-3H-imidazol-1-ium chloride;
3-[3-(2-hydroxy-4-methylphenylsulphamoyl)propyl]-1-methyl-3H-imidazol-1-ium chloride;
3-[3-(2-hydroxy-4-aminophenylsulphamoyl)propyl]-1-methyl-3H-imidazol-1-ium chloride;
3-[3-(2-hydroxy-4-acetylaminophenylsulphamoyl)propyl]-1-methyl-3H-imidazol-1-ium chloride;
3-[3-(2-hydroxy-4-methoxycarbonylaminophenylsulphamoyl)propyl]-1-methyl-3H-imidazol-1-ium chloride;
3-[(3-hydroxy-4-methanesulphonylaminophenylcarbamoyl)methyl]-1-methyl-3H-imidazol-1-ium chloride;
3-[(3-hydroxy-4-benzenesulphonylaminophenylcarbamoyl)methyl]-1-methyl-3H-imidazol-1-ium chloride;
3-[3-(2-hydroxy-5-chlorophenylsulphamoyl)propyl]-1-methyl-3H-imidazol-1-ium chloride;
3-[3-(2-hydroxy-4-methyl-5-chlorophenylsulphamoyl)propyl]-1-methyl-3H-imidazol-1-ium chloride;
3-[3-(2-hydroxy-4-amino-5-chlorophenylsulphamoyl)propyl]-1-methyl-3H-imidazol-1-ium chloride;
3-[3-(2-hydroxy-4-acetylamino-5-chlorophenylsulphamoyl)propyl]-1-methyl-3H-imidazol-1-ium chloride;
3-[3-(2-hydroxy-4-methoxycarbonylamino-5-chlorophenylsulphamoyl)propyl]-1-methyl-3H-imidazol-1-ium chloride;
3-[(3-hydroxy-4-methanesulphonylamino-5-chlorophenylcarbamoyl)methyl]-1-methyl-3H-imidazol-1-ium chloride;
3-[(3-hydroxy-4-benzenesulphonylamino-6-chlorophenylcarbamoyl)methyl]-1-methyl-3H-imidazol-1-ium chloride;
3-[3-(2-hydroxy-5-methoxyphenylsulphamoyl)propyl]-1-methyl-3H-imidazol-1-ium chloride;
3-[3-(2-hydroxy-4-methyl-5-methoxyphenylsulphamoyl)propyl]-1-methyl-3H-imidazol-1-ium chloride;
3-[3-(2-hydroxy-4-amino-5-methoxyphenylsulphamoyl)propyl]-1-methyl-3H-imidazol-1-ium chloride;
3-[3-(2-hydroxy-4-acetylamino-5-methoxyphenylsulphamoyl)propyl]-1-methyl-3H-imidazol-1-ium chloride;
3-[3-(2-hydroxy-4-methoxycarbonylamino-5-methoxyphenylsulphamoyl)propyl]-1-methyl-3H-imidazol-1-ium chloride;
3-[(3-hydroxy-4-methanesulphonylamino-6-methoxyphenylcarbamoyl)methyl]-1-methyl-3H-imidazol-1-ium chloride;
3-[(3-hydroxy-4-benzenesulphonylamino-6-methoxyphenylcarbamoyl)methyl]-1-methyl-3H-imidazol-1-ium chloride;
3-[3-(2-hydroxy-6-aminophenylsulphamoyl)propyl]-1-methyl-3H-imidazol-1-ium chloride;
3-[3-(2-hydroxy-6-acetylaminophenylsulphamoyl)propyl]-1-methyl-3H-imidazol-1-ium chloride;
3-[3-(2-hydroxy-4,6-diaminophenylsulphamoyl)propyl]-1-methyl-3H-imidazol-1-ium chloride;
3-[3-(2-hydroxy-4-acetylamino-6-aminophenylsulphamoyl)propyl]-1-methyl-3H-imidazol-1-ium chloride;
3-[3-(2-hydroxy-3,5-dichloro-4-methylphenylsulphamoyl)propyl]-1-methyl-3H-imidazol-1-ium chloride;
3-[3-(2-hydroxy-3,5-dichloro-4-aminophenylsulphamoyl)propyl]-1-methyl-3H-imidazol-1-ium chloride;
3-[3-(2-hydroxy-3,5-dichloro-4-acetylaminophenylsulphamoyl)propyl]-1-methyl-3H-imidazol-1-ium chloride;
3-[3-(2-hydroxy-3,5-dichloro-4-methoxycarbonylaminophenylsulphamoyl)propyl]-1-methyl-3H-imidazol-1-ium chloride;
3-[3-(2-hydroxy-3-acetylaminophenylsulphamoyl)propyl]-1-methyl-3H-imidazol-1-ium chloride;
1-[3-(2-hydroxyphenylcarbamoyl)methyl]pyridinium chloride;
1-[3-(2-hydroxy-4-methylphenylcarbamoyl)methyl]pyridinium chloride;
1-[3-(2-hydroxy-4-aminophenylcarbamoyl)methyl]pyridinium chloride;
1-[3-(2-hydroxy-4-acetylaminophenylcarbamoyl)methyl]pyridinium chloride;
1-[3-(2-hydroxy-4-methoxycarbonylaminophenylcarbamoyl)methyl]pyridinium chloride;

1-[(3-hydroxy-4-methanesulphonylaminophenylcarbamoyl)
methyl]-pyridinium chloride;
1-[(3-hydroxy-4-benzenesulphonylaminophenylcarbamoyl)
methyl]-pyridinium chloride;
1-[3-(2-hydroxy-5-chlorophenylcarbamoyl)methyl]
pyridinium chloride;
1-[3-(2-hydroxy-4-methyl-5-chlorophenylcarbamoyl)
methyl]pyridinium chloride;
1-[3-(2-hydroxy-4-amino-5-chlorophenylcarbamoyl)
methyl]pyridinium chloride;
1-[3-(2-hydroxy-4-acetylamino-5-chlorophenylcarbamoyl)
methyl]pyridinium chloride;
1-[3-(2-hydroxy-4-methoxycarbonylamino-5-
chlorophenylcarbamoyl)methyl]pyridinium chloride;
1-[(3-hydroxy-4-methanesulphonylamino-6-
chlorophenylcarbamoyl)methyl]pyridinium chloride;
1-[(3-hydroxy-4-benzenesulphonylamino-6-
chlorophenylcarbamoyl)methyl]pyridinium chloride;
1-[3-(2-hydroxy-5-methoxyphenylcarbamoyl)methyl]
pyridinium chloride;
1-[3-(2-hydroxy-4-methyl-5-methoxyphenylcarbamoyl)
methyl]pyridinium chloride;
1-[3-(2-hydroxy-4-amino-5-methoxyphenylcarbamoyl)
methyl]pyridinium chloride;
1-[3-(2-hydroxy-4-acetylamino-5-
methoxyphenylcarbamoyl)methyl]pyridinium chloride;
1-[3-(2-hydroxy-4-methoxycarbonylamino-5-
methoxyphenylcarbamoyl)methyl]pyridinium chloride;
1-[(3-hydroxy-4-methanesulphonylamino-6-
methoxyphenylcarbamoyl)methyl]pyridinium chloride;
1-[(3-hydroxy-4-benzenesulphonylamino-6-
methoxyphenylcarbamoyl)methyl]pyridinium chloride;
1-[3-(2-hydroxy-6-aminophenylcarbamoyl)methyl]
pyridinium chloride;
1-[3-(2-hydroxy-6-acetylaminophenylcarbamoyl)methyl]
pyridinium chloride;
1-[3-(2-hydroxy-4,6-diaminophenylcarbamoyl)methyl]
pyridinium chloride;
1-[3-(2-hydroxy-4-acetylamino-6-aminophenylcarbamoyl)
methyl]pyridinium chloride;
1-[3-(2-hydroxy-3,5-dichloro-4-methylphenylcarbamoyl)
methyl]pyridinium chloride;
1-[3-(2-hydroxy-3,5-dichloro-4-aminophenylcarbamoyl)
methyl]pyridinium chloride;
1-[3-(2-hydroxy-3,5-dichloro-4-
acetylaminophenylcarbamoyl)methyl]pyridinium chloride;
1-[3-(2-hydroxy-3,5-dichloro-4-
methoxycarbonylaminophenylcarbamoyl)methyl]-
pyridinium chloride;
1-[3-(2-hydroxy-3-acetylaminophenylcarbamoyl)methyl]
pyridinium chloride;
1-[3-(2-hydroxyphenylsulphamoyl)propyl]-1,4-
dimethylpiperazin-1-ium chloride;
1-[3-(2-hydroxy-4-methylphenylsulphamoyl)propyl]-1,4-
dimethylpiperazin-1-ium chloride;
1-[3-(2-hydroxy-4-aminophenylsulphamoyl)propyl]-1,4-
dimethylpiperazin-1-ium chloride;
1-[3-(2-hydroxy-4-acetylaminophenylsulphamoyl)propyl]-
1,4-dimethylpiperazin-1-ium chloride;
1-[3-(2-hydroxy-4-
methoxycarbonylaminophenylsulphamoyl)propyl]-1,4-
dimethylpiperazin-1-ium chloride;
1-[(3-hydroxy-4-methanesulphonylaminophenylcarbamoyl)
methyl]-1,4-dimethylpiperazin-1-ium chloride;
1-[(3-hydroxy-4-benzenesulphonylaminophenylcarbamoyl)
methyl]-1,4-dimethylpiperazin-1-ium chloride;
1-[3-(2-hydroxy-5-chlorophenylsulphamoyl)propyl]-1,4-
dimethylpiperazin-1-ium chloride;
1-[3-(2-hydroxy-4-methyl-5-chlorophenylsulphamoyl)
propyl]-1,4-dimethylpiperazin-1-ium chloride;
1-[3-(2-hydroxy-4-amino-5-chlorophenylsulphamoyl)
propyl]-1,4-dimethylpiperazin-1-ium chloride;
1-[3-(2-hydroxy-4-acetylamino-5-chlorophenylsulphamoyl)
propyl]-1,4-dimethylpiperazin-1-ium chloride;
1-[3-(2-hydroxy-4-methoxycarbonylamino-5-
chlorophenylsulphamoyl)propyl]-1,4-dimethylpiperazin-
1-ium chloride;
1-[(3-hydroxy-4-methanesulphonylamino-6-
chlorophenylcarbamoyl)methyl]-1,4-dimethylpiperazin-
1-ium chloride;
1-[(3-hydroxy-4-benzenesulphonylamino-6-
chlorophenylcarbamoyl)methyl]-1,4-dimethylpiperazin-
1-ium chloride;
1-[3-(2-hydroxy-5-methoxyphenylsulphamoyl)propyl]-1,4-
dimethylpiperazin-1-ium chloride;
1-[3-(2-hydroxy-4-methyl-5-methoxyphenylsulphamoyl)
propyl]-1,4-dimethylpiperazin-1-ium chloride;
1-[3-(2-hydroxy-4-amino-5-methoxyphenylsulphamoyl)
propyl]-1,4-dimethylpiperazin-1-ium chloride;
1-[3-(2-hydroxy-4-acetylamino-5-
methoxyphenylsulphamoyl)propyl]-1,4-
dimethylpiperazin-1-ium chloride;
1-[3-(2-hydroxy-4-methoxycarbonylamino-5-
methoxyphenylsulphamoyl)propyl]-1,4-
dimethylpiperazin-1-ium chloride;
1-[(3-hydroxy-4-methanesulphonylamino-6-
methoxyphenylcarbamoyl)methyl]-1,4-
dimethylpiperazin-1-ium chloride;
1-[(3-hydroxy-4-benzenesulphonylamino-6-
methoxyphenylcarbamoyl)methyl]-1,4-
dimethylpiperazin-1-ium chloride;
1-[3-(2-hydroxy-6-aminophenylsulphamoyl)propyl]-1,4-
dimethylpiperazin-1-ium chloride;
1-[3-(2-hydroxy-6-acetylaminophenylsulphamoyl)propyl]-
1,4-dimethylpiperazin-1-ium chloride;
1-[3-(2-hydroxy-4,6-diaminophenylsulphamoyl)propyl]-1,
4-dimethylpiperazin-1-ium chloride;
1-[3-(2-hydroxy-4-acetylamino-6-aminophenylsulphamoyl)
propyl]-1,4-dimethylpiperazin-1-ium chloride;
1-[3-(2-hydroxy-3,5-dichloro-4-methylphenylsulphamoyl)
propyl]-1,4-dimethylpiperazin-1-ium chloride;
1-[3-(2-hydroxy-3,5-dichloro-4-aminophenylsulphamoyl)
propyl]-1,4-dimethylpiperazin-1-ium chloride;
1-[3-(2-hydroxy-3,5-dichloro-4-
acetylaminophenylsulphamoyl)propyl]-1,4-
dimethylpiperazin-1-ium chloride;
1-[3-(2-hydroxy-3,5-dichloro-4-
methoxycarbonylaminophenylsulphamoyl)propyl]-1,4-
dimethylpiperazin-1-ium chloride;
1-[3-(2-hydroxy-3-acetylaminophenylsulphamoyl)propyl]-
1,4-dimethylpiperazin-1-ium chloride;
and acid addition salts thereof.

20. A compound according to any one of claims 1 to 14 and 19, wherein the acid addition salts are chosen from hydrochlorides, hydrobromides, sulphates, citrates, succinates, tartrates, lactates and acetates.

21. A method for oxidation dyeing of keratin fibers, comprising dyeing of the keratin fibers and using as a coupler for the oxidation dyeing at least one compound of formula (I) below and acid addition salts thereof:

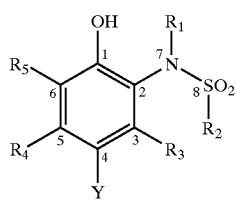

(I)

wherein:
- R₁ represents a hydrogen atom; a group Z as defined below; a linear or branched radical containing from 1 to 15 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an SO₂ group, and the carbon atoms of said radical can, independently of each other, be substituted with one or more halogen atoms, with the proviso that said radical R₁ comprises no peroxide linkages or diazo, nitro or nitroso radicals;
- R₂ represents a hydrogen atom; a group Z as defined below; a linear or branched radical containing from 1 to 20 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an SO₂ group, and the carbon atoms of said radical can, independently of each other, be substituted with one or more halogen atoms; with the proviso that said radical R₂ comprises no peroxide linkages or diazo, nitro or nitroso radicals;
- R₃, R₄ and R₅, which may be identical or different, represent a hydrogen or halogen atom; a group Z as defined below; a linear or branched radical containing from 1 to 20 carbon atoms, wherein the branch(es) may form one or more 3- to 7-membered rings and wherein said radical can contain one or more double bonds and/or one or more triple bonds, wherein said double bonds may optionally lead to one or more aromatic groups, and one or more carbon atoms of said radical can be replaced with an oxygen, nitrogen or sulphur atom or with an SO₂ group, and the carbon atoms of said radical can, independently of each other, be substituted with one or more halogen atoms; with the provisos that said radicals R₃, R₄ and R₅ comprise no peroxide linkages or diazo, nitro or nitroso radicals; R₅ cannot represent a hydroxyl, thio or amino radical; and the radicals R₃, R₄ and R₅ cannot be linked to the benzene ring of formula (I) via an —NH—NH— linkage;
- Y represents a hydrogen or halogen atom; a group —OR₆, —SR₆ or —NH—SO₂R₆ in which R₆ represents a linear or branched C₁–C₆ alkyl radical, wherein the branch(es) may form one or more 3- to 6-membered rings and wherein said linear or branched C₁–C₆ alkyl radical optionally may be substituted with one or more radicals chosen from the group: halogen, hydroxyl, C₁–C₄ alkoxy, amino, C₁–C₄ aminoalkyl; a phenyl radical, optionally substituted with one or two radicals chosen from the group: C₁–C₄ alkyl, trifluoromethyl, carboxyl, (C₁–C₄)alkoxycarbonyl, halogen, hydroxyl, C₁–C₄ alkoxy, amino, C₁–C₄ aminoalkyl; a benzyl radical;
- Z represents a cationic group represented by formula (II) below:

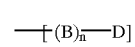

(II)

wherein:
- represents a linear or branched C₁–C₁₅ alkyl radical, wherein the branch(es) may form one or more 3- to 7-membered rings, and wherein said linear or branched C₁–C₁₅ alkyl radical can contain one or more double bonds and/or one or more triple bonds, wherein said double bonds may optionally lead to one or more aromatic groups, and wherein one or more carbon atoms of said linear or branched C₁–C₁₅ alkyl radical can be replaced with an oxygen, nitrogen or sulphur atom or with an SO₂ radical; and one or more carbon atoms of said linear or branched C₁–C₁₅ alkyl radical can, independently of each other, be substituted with one or more halogen atoms or with one or more groups Z; with the proviso that B comprises no peroxide linkages or diazo, nitro or nitroso radicals;
- D is chosen from the groups of formulae (III) and (IV) below:

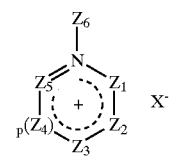

(III)

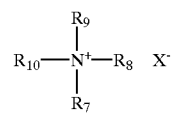

(IV)

wherein:
- the radical B is linked to the group D by any of the atoms in the radical D;
- n and p can, independently of each other, take the value 0 or 1;
- when n=0, then the group (IV) can be linked to the compound of formula (I) directly via the nitrogen of the quaternary ammonium, in place of the radical R₁₀;
- Z₁, Z₂, Z₃ and Z₄, independently of each other, represent an oxygen atom; a sulphur atom; a nitrogen atom which is unsubstituted or substituted with a radical R₁₁; a carbon atom which is unsubstituted or substituted with one or two radicals R₁₁, which may be identical or different;
- Z₅ represents a nitrogen atom; a carbon atom which is unsubstituted or substituted with a radical R₁₁;
- Z₆ can take the same meanings as those indicated below for the radical R₁₁; with the proviso that Z₆ is not a hydrogen atom;
- in addition, the radicals Z₁ or Z₅ can form, with Z₆, a saturated or unsaturated 5- to 7-membered ring, each ring member being unsubstituted or substituted with one or two radicals $R_{11}$, which may be identical or different;

$R_{11}$ represents a hydrogen atom; a group Z; a linear or branched radical containing from 1 to 10 carbon atoms which can contain one or more double bonds and/or one or more triple bonds, wherein said double bonds may optionally lead to one or more aromatic groups, and wherein one or more carbon atoms of said linear or branched radical can be replaced with an oxygen, nitrogen or sulphur atom or with an $SO_2$ group, and one or more carbon atoms of said linear or branched radical can, independently of each other, be substituted with one or more halogen atoms, with the proviso that said $R_{11}$ comprises no peroxide linkages and no diazo, nitro or nitroso radicals;

two of the adjacent radicals $Z_1$, $Z_2$, $Z_3$, $Z_4$ and $Z_5$ can also form a 5- to 7-membered ring, each ring member being independently represented by:

a carbon atom which is unsubstituted or substituted with one or two radicals $R_{11}$, which may be identical or different;

a nitrogen atom which is unsubstituted or substituted with a radical $R_{11}$;

an oxygen atom;

a sulphur atom;

$R_7$, $R_8$, $R_9$ and $R_{10}$, which may be identical or different, have the same meanings as those indicated above for the radical $R_{11}$;

the radicals $R_7$, $R_8$ and $R_9$ can also form, in pairs with the quaternary nitrogen atom to which they are attached, one or more saturated 5- to 7-membered rings, each ring member being independently represented by:

a carbon atom which is unsubstituted or substituted with one or two radicals $R_{11}$, which may be identical or different;

a nitrogen atom which is unsubstituted or substituted with a radical $R_{11}$;

an oxygen atom;

a sulphur atom;

$X^-$ represents an organic or inorganic anion;

with the proviso that at least one of the groups $R_1$ to $R_5$ represents a group Z.

22. A composition for the oxidation dyeing of keratin fibres, comprising, in a medium which is suitable for dyeing:

at least one oxidation base, and at least one coupler chosen from a compound of formula (I) below and acid addition salts thereof:

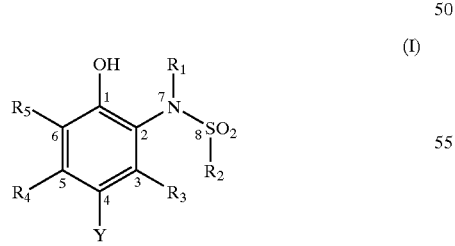

(I)

wherein:

$R_1$ represents a hydrogen atom; a group Z as defined below; a linear or branched radical containing from 1 to 15 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an $SO_2$ group, and the carbon atoms of said radical can, independently of each other, be substituted with one or more halogen atoms, with the proviso that said radical $R_1$ comprises no peroxide linkages or diazo, nitro or nitroso radicals;

$R_2$ represents a hydrogen atom; a group Z as defined below; a linear or branched radical containing from 1 to 20 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an $SO_2$ group, and the carbon atoms of said radical can, independently of each other, be substituted with one or more halogen atoms; with the proviso that said radical $R_2$ comprises no peroxide linkages or diazo, nitro or nitroso radicals;

$R_3$, $R_4$ and $R_5$, which may be identical or different, represent a hydrogen or halogen atom; a group Z as defined below; a linear or branched radical containing from 1 to 20 carbon atoms, wherein the branch(es) may form one or more 3- to 7-membered rings and wherein said radical can contain one or more double bonds and/or one or more triple bonds, wherein said double bonds may optionally lead to one or more aromatic groups, and one or more carbon atoms of said radical can be replaced with an oxygen, nitrogen or sulphur atom or with an $SO_2$ group, and the carbon atoms of said radical can, independently of each other, be substituted with one or more halogen atoms; with the provisos that said radicals $R_3$, $R_4$ and $R_5$ comprise no peroxide linkages or diazo, nitro or nitroso radicals; $R_5$ cannot represent a hydroxyl, thio or amino radical; and the radicals $R_3$, $R_4$ and $R_5$ cannot be linked to the benzene ring of formula (I) via an —NH—NH— linkage;

Y represents a hydrogen or halogen atom; a group —$OR_6$, —$SR_6$ or —NH—$SO_2R_6$ in which $R_6$ represents a linear or branched $C_1$–$C_6$ alkyl radical, wherein the branch(es) may form one or more 3- to 6-membered rings and wherein said linear or branched $C_1$–$C_6$ alkyl radical optionally may be substituted with one or more radicals chosen from the group: halogen, hydroxyl, $C_1$–$C_4$ alkoxy, amino, $C_1$–$C_4$ aminoalkyl; a phenyl radical, optionally substituted with one or two radicals chosen from the group: $C_1$–$C_4$ alkyl, trifluoromethyl, carboxyl, ($C_1$–$C_4$)alkoxycarbonyl, halogen, hydroxyl, $C_1$–$C_4$ alkoxy, amino, $C_1$–$C_4$ aminoalkyl; a benzyl radical; represents a cationic group represented by formula (II) below:

(II)

wherein:

B represents a linear or branched $C_1$–$C_{15}$ alkyl radical, wherein the branch(es) may form one or more 3- to 7-membered rings, and wherein said linear or branched $C_1$–$C_{15}$ alkyl radical can contain one or more double bonds and/or one or more triple bonds, wherein said double bonds may optionally lead to one or more aromatic groups, and wherein one or more carbon atoms of said linear or branched $C_1$–$C_{15}$ alkyl radical can be replaced with an oxygen, nitrogen or sulphur atom or with an $SO_2$ radical; and one or more carbon atoms of said linear or branched $C_1$–$C_{15}$ alkyl radical can, independently of each other, be substituted with one or more halogen atoms or with one or more groups Z; with the proviso that B comprises no peroxide linkages or diazo, nitro or nitroso radicals;

D is chosen from the groups of formulae (III) and (IV) below:

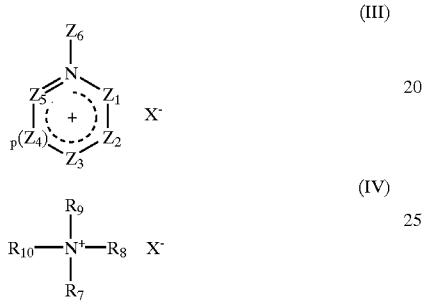

wherein:
- the radical B is linked to the group D by any of the atoms in the radical D;
- n and p can, independently of each other, take the value 0 or 1;
- when n=0, then the group (IV) can be linked to the compound of formula (I) directly via the nitrogen of the quaternary ammonium, in place of the radical $R_{10}$;
- $Z_1$, $Z_2$, $Z_3$ and $Z_4$, independently of each other, represent an oxygen atom; a sulphur atom; a nitrogen atom which is unsubstituted or substituted with a radical $R_{11}$; a carbon atom which is unsubstituted or substituted with one or two radicals $R_{11}$, which may be identical or different;
- $Z_5$ represents a nitrogen atom; a carbon atom which is unsubstituted or substituted with a radical $R_{11}$;
- $Z_6$ can take the same meanings as those indicated below for the radical $R_{11}$; with the proviso that $Z_6$ is not a hydrogen atom;
- in addition, the radicals $Z_1$ or $Z_5$ can form, with $Z_6$, a saturated or unsaturated 5- to 7-membered ring, each ring member being unsubstituted or substituted with one or two radicals $R_{11}$, which may be identical or different;
- $R_{11}$ represents a hydrogen atom; a group Z; a linear or branched radical containing from 1 to 10 carbon atoms which can contain one or more double bonds and/or one or more triple bonds, wherein said double bonds may optionally lead to one or more aromatic groups, and wherein one or more carbon atoms of said linear or branched radical can be replaced with an oxygen, nitrogen or sulphur atom or with an $SO_2$ group, and one or more carbon atoms of said linear or branched radical can, independently of each other, be substituted with one or more halogen atoms, with the proviso that said $R_{11}$ comprises no peroxide linkages and no diazo, nitro or nitroso radicals;
- two of the adjacent radicals $Z_1$, $Z_2$, $Z_3$, $Z_4$ and $Z_5$ can also form a 5- to 7-membered ring, each ring member being independently represented by:
  - a carbon atom which is unsubstituted or substituted with one or two radicals $R_{11}$, which may be identical or different;
  - a nitrogen atom which is unsubstituted or substituted with a radical $R_{11}$;
  - an oxygen atom;
  - a sulphur atom;
- $R_7$, $R_8$, $R_9$ and $R_{10}$, which may be identical or different, have the same meanings as those indicated above for the radical $R_{11}$;
- the radicals $R_7$, $R_8$ and $R_9$ can also form, in pairs with the quaternary nitrogen atom to which they are attached, one or more saturated 5- to 7-membered rings, each ring member being independently represented by:
  - a carbon atom which is unsubstituted or substituted with one or two radicals $R_{11}$, which may be identical or different;
  - a nitrogen atom which is unsubstituted or substituted with a radical $R_{11}$;
  - an oxygen atom;
  - a sulphur atom;
- $X^-$ represents an organic or inorganic anion;

with the proviso that at least one of the groups $R_1$ to $R_5$ represents a group Z.

23. A composition according to claim 22, wherein the at least one coupler represents from 0.0005% to 12% by weight relative to the total weight of the dye composition.

24. A composition according to claim 22, wherein the at least one oxidation base is chosen from para-phenylenediamines, bis(phenyl)alkylenediamines, para-aminophenols, ortho-aminophenols and heterocyclic bases, and the acid addition salts thereof.

25. A composition according to claim 22, wherein the at least one oxidation bases represents from 0.0005% to 12% by weight relative to the total weight of the dye composition.

26. A composition according to claim 22, further comprising at least one additional coupler chosen from meta-phenylenediamines, meta-aminophenols, meta-diphenols and heterocyclic coupler, and the acid addition salts thereof, and/or one or more direct dyes.

27. A composition according to claim 26, wherein the at least one additional coupler represents from 0.0001% to 10% by weight relative to the total weight of the dye composition.

28. A composition according to claim 22, wherein the acid addition salts are chosen from hydrochlorides, hydrobromides, sulphates, citrates, succinates, tartrates, lactates and acetates.

29. A process for the oxidation dyeing of keratin fibres, comprising applying at least one dye composition to said fibres, wherein the at least one composition comprises, in a medium which is suitable for dyeing:
- at least one oxidation base, and
- at least one coupler chosen from a compound of formula (I) below and acid addition salts thereof:

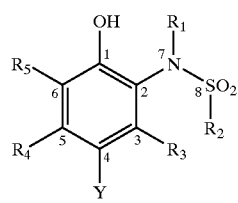

(I)

wherein:
R₁ represents a hydrogen atom; a group Z as defined below; a linear or branched radical containing from 1 to 15 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an SO₂ group, and the carbon atoms of said radical can, independently of each other, be substituted with one or more halogen atoms, with the proviso that said radical R₁ comprises no peroxide linkages or diazo, nitro or nitroso radicals;

R₂ represents a hydrogen atom; a group Z as defined below; a linear or branched radical containing from 1 to 20 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an SO₂ group, and the carbon atoms of said radical can, independently of each other, be substituted with one or more halogen atoms; with the proviso that said radical R₂ comprises no peroxide linkages or diazo, nitro or nitroso radicals;

R₃, R₄ and R₅, which may be identical or different, represent a hydrogen or halogen atom; a group Z as defined below; a linear or branched radical containing from 1 to 20 carbon atoms, wherein the branch(es) may form one or more 3- to 7-membered rings and wherein said radical can contain one or more double bonds and/or one or more triple bonds, wherein said double bonds may optionally lead to one or more aromatic groups, and one or more carbon atoms of said radical can be replaced with an oxygen, nitrogen or sulphur atom or with an SO₂ group, and the carbon atoms of said radical can, independently of each other, be substituted with one or more halogen atoms; with the provisos that said radicals R₃, R₄ and R₅ comprise no peroxide linkages or diazo, nitro or nitroso radicals; R₅ cannot represent a hydroxyl, thio or amino radical; and the radicals R₃, R₄ and R₅ cannot be linked to the benzene ring of formula (I) via an —NH—NH— linkage;

represents a hydrogen or halogen atom; a group —OR₆, —SR₆ or —NH—SO₂R₆ in which R₆ represents a linear or branched C₁–C₆ alkyl radical, wherein the branch(es) may form one or more 3- to 6-membered rings and wherein said linear or branched C₁–C₆ alkyl radical optionally may be substituted with one or more radicals chosen from the group: halogen, hydroxyl, C₁–C₄ alkoxy, amino, C₁–C₄ aminoalkyl; a phenyl radical, optionally substituted with one or two radicals chosen from the group: C₁–C₄ alkyl, trifluoromethyl, carboxyl, (C₁–C₄)alkoxycarbonyl, halogen, hydroxyl, C₁–C₄ alkoxy, amino, C₁–C₄ aminoalkyl; a benzyl radical;

Z represents a cationic group represented by formula (II) below:

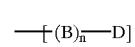

(II)

wherein:
represents a linear or branched C₁–C₁₅ alkyl radical, wherein the branch(es) may form one or more 3- to 7-membered rings, and wherein said linear or branched C₁–C₁₅ alkyl radical can contain one or more double bonds and/or one or more triple bonds, wherein said double bonds may optionally lead to one or more aromatic groups, and wherein one or more carbon atoms of said linear or branched C₁–C₁₅ alkyl radical can be replaced with an oxygen, nitrogen or sulphur atom or with an SO₂ radical; and one or more carbon atoms of said linear or branched C₁–C₁₅ alkyl radical can, independently of each other, be substituted with one or more halogen atoms or with one or more groups Z; with the proviso that B comprises no peroxide linkages or diazo, nitro or nitroso radicals;

D is chosen from the groups of formulae (III) and (IV) below:

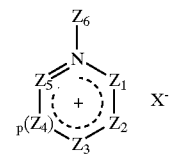

(III)

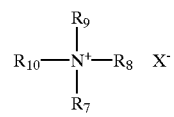

(IV)

wherein:
the radical B is linked to the group D by any of the atoms in the radical D;
n and p can, independently of each other, take the value 0 or 1;
when n=0, then the group (IV) can be linked to the compound of formula (I) directly via the nitrogen of the quaternary ammonium, in place of the radical R₁₀;
Z₁, Z₂, Z₃ and Z₄, independently of each other, represent an oxygen atom; a sulphur atom; a nitrogen atom which is unsubstituted or substituted with a radical R₁₁; a carbon atom which is unsubstituted or substituted with one or two radicals R₁₁, which may be identical or different;
Z₅ represents a nitrogen atom; a carbon atom which is unsubstituted or substituted with a radical R₁₁;
Z₆ can take the same meanings as those indicated below for the radical R₁ ; with the proviso that Z₆ is not a hydrogen atom;

in addition, the radicals $Z_1$ or $Z_5$ can form, with $Z_6$, a saturated or unsaturated 5- to 7-membered ring, each ring member being unsubstituted or substituted with one or two radicals $R_{11}$, which may be identical or different;

$R_{11}$ represents a hydrogen atom; a group Z; a linear or branched radical containing from 1 to 10 carbon atoms which can contain one or more double bonds and/or one or more triple bonds, wherein said double bonds may optionally lead to one or more aromatic groups, and wherein one or more carbon atoms of said linear or branched radical can be replaced with an oxygen, nitrogen or sulphur atom or with an $SO_2$ group, and one or more carbon atoms of said linear or branched radical can, independently of each other, be substituted with one or more halogen atoms, with the proviso that said $R_{11}$ comprises no peroxide linkages and no diazo, nitro or nitroso radicals;

two of the adjacent radicals $Z_1$, $Z_2$, $Z_3$, $Z_4$ and $Z_5$ can also form a 5- to 7-membered ring, each ring member being independently represented by:
 a carbon atom which is unsubstituted or substituted with one or two radicals $R_{11}$, which may be identical or different;
 a nitrogen atom which is unsubstituted or substituted with a radical $R_{11}$;
 an oxygen atom;
 a sulphur atom;

$R_7$, $R_8$, $R_9$ and $R_1$, which may be identical or different, have the same meanings as those indicated above for the radical $R_{11}$;

the radicals $R_7$, $R_8$ and $R_9$ can also form, in pairs with the quaternary nitrogen atom to which they are attached, one or more saturated 5- to 7-membered rings, each ring member being independently represented by:
 a carbon atom which is unsubstituted or substituted with one or two radicals $R_{11}$, which may be identical or different;
 a nitrogen atom which is unsubstituted or substituted with a radical $R_{11}$;
 an oxygen atom;
 a sulphur atom;

$X^-$ represents an organic or inorganic anion;

with the proviso that at least one of the groups $R_1$ to $R_5$ represents a group Z; and developing a colour at acidic, neutral or alkaline pH using an oxidizing agent which is added to the dye composition just at the time of use, or which is present in an oxidizing composition applied simultaneously or sequentially in a separate manner.

30. A process according to claim 29, wherein the oxidizing agent is chosen from hydrogen peroxide, urea peroxide, alkali metal bromates, persalts and enzymes.

31. A multi-compartment device or multi-compartment dyeing "kit", comprising a first compartment comprising a dye composition, and a second compartment comprising an oxidizing composition, wherein the dye composition comprises, in a medium which is suitable for dyeing:
 at least one oxidation base, and
 at least one coupler chosen from a compound of formula (I) below and acid addition salts thereof:

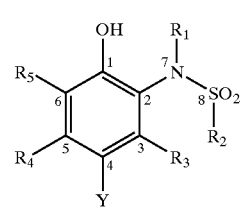

wherein:

$R_1$ represents a hydrogen atom; a group Z as defined below; a linear or branched radical containing from 1 to 15 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an $SO_2$ group, and the carbon atoms of said radical can, independently of each other, be substituted with one or more halogen atoms, with the proviso that said radical $R_1$ comprises no peroxide linkages or diazo, nitro or nitroso radicals;

$R_2$ represents a hydrogen atom; a group Z as defined below; a linear or branched radical containing from 1 to 20 carbon atoms wherein the branch(es) may form one or more 3- to 7-membered carbon-based rings and wherein said radical can contain one or more double bonds and/or one or more triple bonds, wherein said double bonds may optionally lead to one or more aromatic groups, and wherein one or more carbon atoms of said radical can be replaced with an oxygen, nitrogen or sulphur atom or with an $SO_2$ group, and the carbon atoms of said radical can, independently of each other, be substituted with one or more halogen atoms; with the proviso that said radical $R_2$ comprises no peroxide linkages or diazo, nitro or nitroso radicals;

$R_3$, $R_4$ and $R_5$, which may be identical or different, represent a hydrogen or halogen atom; a group Z as defined below; a linear or branched radical containing from 1 to 20 carbon atoms, wherein the branch(es) may form one or more 3- to 7-membered rings and wherein said radical can contain one or more double bonds and/or one or more triple bonds, wherein said double bonds may optionally lead to one or more aromatic groups, and one or more carbon atoms of said radical can be replaced with an oxygen, nitrogen or sulphur atom or with an $SO_2$ group, and the carbon atoms of said radical can, independently of each other, be substituted with one or more halogen atoms; with the provisos that said radicals $R_3$, $R_4$ and $R_5$ comprise no peroxide linkages or diazo, nitro or nitroso radicals; $R_5$ cannot represent a hydroxyl, thio or amino radical; and the radicals $R_3$, $R_4$ and $R_5$ cannot be linked to the benzene ring of formula (I) via an —NH—NH— linkage;

Y represents a hydrogen or halogen atom; a group —$OR_6$, —$SR_6$ or —NH—$SO_2R_6$ in which $R_6$ represents a linear or branched $C_1$–$C_6$ alkyl radical, wherein the branch(es) may form one or more 3- to 6-membered rings and wherein said linear or branched $C_1$–$C_6$ alkyl radical optionally may be substituted with one or more radicals chosen from the group: halogen, hydroxyl, $C_1$–$C_4$ alkoxy, amino, $C_1$–$C_4$ aminoalkyl; a phenyl radical, optionally substituted with one or two radicals chosen from the group: $C_1$–$C_4$ alkyl, trifluoromethyl, carboxyl, ($C_1$–$C_4$)alkoxycarbonyl, halogen, hydroxyl, $C_1$–$C_4$ alkoxy, amino, $C_1$–$C_4$ aminoalkyl; a benzyl radical;

p2 Z represents a cationic group represented by formula (II) below:

(II)

wherein:
B represents a linear or branched $C_1$–$C_{15}$ alkyl radical, wherein the branch(es) may form one or more 3- to 7-membered rings, and wherein said linear or branched $C_1$–$C_{15}$ alkyl radical can contain one or more double bonds and/or one or more triple bonds, wherein said double bonds may optionally lead to one or more aromatic groups, and wherein one or more carbon atoms of said linear or branched $C_1$–$C_{15}$ alkyl radical can be replaced with an oxygen, nitrogen or sulphur atom or with an $SO_2$ radical; and one or more carbon atoms of said linear or branched $C_1$–$C_{15}$ alkyl radical can, independently of each other, be substituted with one or more halogen atoms or with one or more groups Z; with the proviso that B comprises no peroxide linkages or diazo, nitro or nitroso radicals;

D is chosen from the groups of formulae (III) and (IV) below:

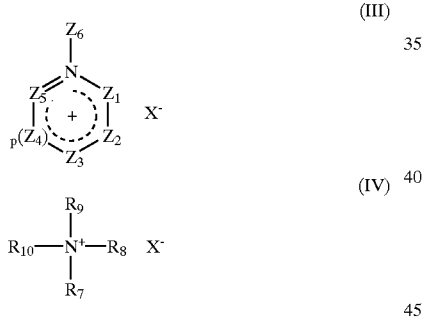

wherein:
the radical B is linked to the group D by any of the atoms in the radical D;
n and p can, independently of each other, take the value 0 or 1;
when n=0, then the group (IV) can be linked to the compound of formula (I) directly via the nitrogen of the quaternary ammonium, in place of the radical $R_{10}$;
$Z_1$, $Z_2$, $Z_3$ and $Z_4$, independently of each other, represent an oxygen atom; a sulphur atom; a nitrogen atom which is unsubstituted or substituted with a radical $R_{11}$; a carbon atom which is unsubstituted or substituted with one or two radicals $R_{11}$, which may be identical or different;
$Z_5$ represents a nitrogen atom; a carbon atom which is unsubstituted or substituted with a radical $R_{11}$;

$Z_6$ can take the same meanings as those indicated below for the radical $R_{11}$; with the proviso that $Z_6$ is not a hydrogen atom;
in addition, the radicals $Z_1$ or $Z_5$ can form, with $Z_6$, a saturated or unsaturated 5- to 7-membered ring, each ring member being unsubstituted or substituted with one or two radicals $R_{11}$, which may be identical or different;
$R_{11}$ represents a hydrogen atom; a group Z; a linear or branched radical containing from 1 to 10 carbon atoms which can contain one or more double bonds and/or one or more triple bonds, wherein said double bonds may optionally lead to one or more aromatic groups, and wherein one or more carbon atoms of said linear or branched radical can be replaced with an oxygen, nitrogen or sulphur atom or with an $SO_2$ group, and one or more carbon atoms of said linear or branched radical can, independently of each other, be substituted with one or more halogen atoms, with the proviso that said $R_{11}$ comprises no peroxide linkages and no diazo, nitro or nitroso radicals;
two of the adjacent radicals $Z_1$, $Z_2$, $Z_3$, $Z_4$ and $Z_5$ can also form a 5- to 7-membered ring, each ring member being independently represented by:
a carbon atom which is unsubstituted or substituted with one or two radicals $R_{11}$, which may be identical or different;
a nitrogen atom which is unsubstituted or substituted with a radical $R_{11}$;
an oxygen atom;
a sulphur atom;
$R_7$, $R_8$, $R_9$ and $R_{10}$, which may be identical or different, have the same meanings as those indicated above for the radical $R_{11}$;
the radicals $R_7$, $R_8$ and $R_9$ can also form, in pairs with the quaternary nitrogen atom to which they are attached, one or more saturated 5- to 7-membered rings, each ring member being independently represented by:
a carbon atom which is unsubstituted or substituted with one or two radicals $R_{11}$, which may be identical or different;
a nitrogen atom which is unsubstituted or substituted with a radical $R_{11}$;
an oxygen atom;
a sulphur atom;
$X^-$ represents an organic or inorganic anion;
with the proviso that at least one of the groups $R_1$ to $R_5$ represents a group Z.

32. A composition according to claim 24, wherein the acid addition salts are chosen from hydrochlorides, hydrobromides, sulphates, citrates, succinates, tartrates, lactates and acetates.

33. A composition according to claim 26, wherein the acid addition salts are chosen from hydrochlorides, hydrobromides, sulphates, citrates, succinates, tartrates, lactates and acetates.

* * * * *

UNITED STATES PATENT AND TRADEMARK OFFICE
CERTIFICATE OF CORRECTION

PATENT NO. : 6,537,329 B1  Page 1 of 2
DATED : March 25, 2003
INVENTOR(S) : Laurent Vidal et al.

It is certified that error appears in the above-identified patent and that said Letters Patent is hereby corrected as shown below:

Title page,
Item [75], Inventors, "Jean-Baptise" should read -- Jean-Baptiste --.

Column 23,
Lines 7 and 22, "A compounds" should read -- A compound --.
Line 21, "-N-($C_1$-$C_3$)alkyl-group" should read -- -N-($C_1$-$C_3$)alkyl- group --.
Lines 37-38, "tri(C1-C4)alkylammonium-N-yl," should read -- tri($C_1$-$C_4$) alkylammonium-N-yl, --.

Column 24,
Line 8, "2-methyl-5-phenylfur-3-thien-2-yl," should read -- 2-methyl-5-phenylfur-3-yl, thien-2-yl, --.
Lines 65-66, "tri(C1-C4)alkylammonium-N-yl," should read -- tri($C_1$-$C_4$) alkylammonium-N-yl, --.

Column 27,
Line 34, "-NHSO2$R_{19}$" should read -- -NHSO$_2$$R_{19}$ --.

Column 28,
Lines 29-30, "N-(C1-C4)alkylpyrid-2-yl, N-(C1-C4)alkylpyrid-3-yl,N-(C1-C4)alkylpyrid-4-yl," should read -- N-($C_1$-$C_4$)alkylpyrid-2-yl, N-($C_1$-$C_4$)alkylpyrid-3-yl,N-($C_1$-$C_4$)alkylpyrid-4-yl, --.
Lines 32-33, "(C1-C4)trialkylammonium-N-yl," should read -- ($C_1$-$C_4$) trialkylammonium-N-yl, --.

Column 29,
Line 49, "N-($C_{1-C4}$)alkylpyrid-4-yl," should read -- N-($C_1$-$C_4$)alkylpyrid-4-yl, --.
Lines 51-52, "tri(C1-C4)alkylammonium-N-yl," should read -- tri($C_1$-$C_4$) alkylammonium-N-yl, --.

Column 34,
Line 13, before "represents a linear", insert -- B --.

Column 36,
Lines 28-29, "branch (es)" should read -- branch(es) --.
Line 58, before "represents a cationic", insert -- Z --.

UNITED STATES PATENT AND TRADEMARK OFFICE
CERTIFICATE OF CORRECTION

PATENT NO. : 6,537,329 B1
DATED : March 25, 2003
INVENTOR(S) : Laurent Vidal et al.

It is certified that error appears in the above-identified patent and that said Letters Patent is hereby corrected as shown below:

Column 38,
Line 44, "one oxidation bases" should read -- one oxidation base --.

Column 39,
Lines 45-46, "branch (es)" should read -- branch(es) --.
Line 62, before "represents a hydrogen", insert -- Y --.

Column 40,
Line 15, before "represents a linear", insert -- B --.
Line 66, "radical $R_1$;" should read -- radical $R_{11}$; --.

Column 41,
Line 32, "$R_1$," should read -- $R_{10}$, --.

Column 42,
Lines 45-46, "branch (es)" should read -- branch(es) --.

Column 43,
Line 8, before "Z represents", delete "p2".

Signed and Sealed this

Sixteenth Day of December, 2003

JAMES E. ROGAN
*Director of the United States Patent and Trademark Office*